US012807596B2

(12) United States Patent
Kim et al.

(10) Patent No.: US 12,807,596 B2
(45) Date of Patent: Nov. 24, 2026

(54) QUERCETIN REDOX DERIVATIVE AND USE THEREOF AS BET INHIBITOR

(71) Applicant: Benobio Co., Ltd., Seongnam-si (KR)

(72) Inventors: Sung Oog Kim, Seoul (KR); Jae Hyuk Choi, Gyeonggi-do (KR); Jae Yeon Lee, Gyeonggi-do (KR); Young Shik Park, Gyeonggi-do (KR); Chang Joong Kim, Gyeonggi-do (KR); Udell Gutterman Jordan, Houston, TX (US); In-Hyun Lee, Gyeonggi-do (KR)

(73) Assignee: Benobio Co., Ltd., Seongnam-si (KR)

( * ) Notice: Subject to any disclaimer, the term of this patent is extended or adjusted under 35 U.S.C. 154(b) by 1113 days.

(21) Appl. No.: 17/780,083

(22) PCT Filed: Nov. 26, 2020

(86) PCT No.: PCT/KR2020/017008
§ 371 (c)(1),
(2) Date: Jan. 27, 2023

(87) PCT Pub. No.: WO2021/107656
PCT Pub. Date: Jun. 3, 2021

(65) Prior Publication Data

US 2023/0053152 A1 Feb. 16, 2023

(30) Foreign Application Priority Data

Nov. 26, 2019 (KR) ........................ 10-2019-0152890

(51) Int. Cl.
*C07D 405/04* (2006.01)
*C07D 407/04* (2006.01)
*C07D 413/04* (2006.01)

(52) U.S. Cl.
CPC ......... *C07D 405/04* (2013.01); *C07D 407/04* (2013.01); *C07D 413/04* (2013.01)

(58) Field of Classification Search
CPC .................................................... C07D 405/04
See application file for complete search history.

(56) References Cited

U.S. PATENT DOCUMENTS

2013/0281396 A1 10/2013 Mclure et al.
2018/0104245 A1 4/2018 Hansen
2018/0353462 A1 12/2018 Lowe et al.

FOREIGN PATENT DOCUMENTS

| | | | |
|---|---|---|---|
| CN | 108289957 | A | 7/2018 |
| JP | S61137818 | A | 6/1986 |
| JP | 1988002925 | A | 1/1988 |
| JP | 2009502970 | A | 1/2009 |
| JP | 2010053067 | A | 3/2010 |
| JP | 2012514631 | A | 6/2012 |
| KR | 20110006083 | A | 1/2011 |
| KR | 20140088893 | A | 7/2014 |
| KR | 20210065883 | A | 6/2021 |
| WO | 2006024545 | A1 | 3/2006 |
| WO | 2013156869 | A1 | 10/2013 |
| WO | 2013186612 | A1 | 12/2013 |
| WO | 2015015318 | A2 | 2/2015 |
| WO | 2018204830 | A2 | 11/2018 |

OTHER PUBLICATIONS

Shoba et al (2017) : STN International, CAPLUS database, Accession No. 22022 : 955717.*
Babu, et al., "An Expeditious Synthesis of Flavonols Promoted by Montmorillonite KSF Clay and Assisted by Microwave Irradiation under Solvent-Free Conditions", Helvetica Chimica Acta—vol. 96 (2013), pp. 1269-1272.
Belkina, et al., "BET domain co-regulators in obesity, inflammation and cancer", Nature Reviews Cancer, vol. 12, Jul. 2012, pp. 465-477.
Cotelle, et al., "Antioxidant Properties of Hydroxy-Flavones", Free Radical Biology & Medicine, vol. 20, No. 1, pp. 35-43 (1996).
Demetzos, Costas, "Antiamoebic and antigiardial activity of plant flavonoids", Planta Med., vol. 65, Jan. 1, 1999, pp. 78-80, XP093092308.
Hussong, et al., "The bromodomain protein BRD4 regulates the KEAP1/NRF2-dependent oxidative stress response", Cell Death and Disease (2014) 5, e1195, 12 pages.
Li, et al., "Dihydrofisetin exerts its anti-inflammatory effects associated with suppressing ERK/p38 MAPK and Heme Oxygenase-1 activation in lipopolysaccharide-stimulated RAW 264.7 macrophages and carrageenan-induced mice paw edema", International Immunopharmacology 54 (2018) 366-374.
Liu, et al., "Discovery of Orally Bioavailable Chromone Derivatives as Potent and Selective BRD4 Inhibitors: Scaffold Hopping, Optimization, and Pharmacological Evaluation", J. Med. Chem. 2020, 63, 5242-5256.

(Continued)

*Primary Examiner* — Golam M Shameem
(74) *Attorney, Agent, or Firm* — SERVILLA WHITNEY LLC

(57) ABSTRACT

The present invention relates to a novel quercetin derivative compound and to a use thereof. More specifically, the present invention relates to a novel quercetin derivative compound having inhibitory activity against bromodomain extra-terminal (BET) proteins, and to a pharmaceutical composition for preventing or treating BET protein-related diseases, comprising the same.

2 Claims, 2 Drawing Sheets

(56) References Cited

OTHER PUBLICATIONS

Michaeloudes, et al., "Bromodomain and Extraterminal Proteins Suppress NF-E2-Related Factor 2-Mediated Antioxidant Gene Expression", The Journal of Immunology 2014; 192:4913-4920.
Pham, et al., "Quercetin Enhances the Anti-Tumor Effects of BET Inhibitors by Suppressing hnRNPA1", Int. J. Mol. Sci. 2019, 20, 4293.
Znati, et al., "Synthesis, molecular properties, anti-inflammatory and anticancer activities of novel 3-hydroxyflavone derivatives", Bioorganic Chemistry 89 (2019) 103009.

* cited by examiner

QUERCETIN REDOX DERIVATIVE AND USE THEREOF AS BET INHIBITOR

CROSS-REFERENCE TO RELATED APPLICATIONS

This application is a National Phase entry of International Application No. PCT/KR2020/017008, filed on Nov. 26, 2020, which claims priority to Korean Application Serial No. 10-2019-0152890, filed on Nov. 26, 2019, the disclosures of which are hereby incorporated herein by reference in their entireties.

TECHNICAL FIELD

The present invention relates to a quercetin derivative or a pharmaceutically acceptable salt thereof, and to a pharmaceutical composition for preventing or treating bromodomain extra-terminal (BET) protein-related diseases, comprising the same as an active ingredient.

BACKGROUND ART

Post-translational modification (PTM) of histones is involved in the regulation of gene expression and chromatin organization in eukaryotic cells. Histone acetylation at specific lysine residues is a PTM regulated by histone acetylases and histone deacetylases. Histone acetylation controls gene expression by recruiting protein complexes by direct binding of well-conserved proteins called bromodomains to acetylated lysines in histones and other proteins. There are more than 60 bromodomain containing proteins in the human genome.

Among bromodomain containing proteins, the bromodomain extra-terminal (BET) family includes BRD2, BRD3, BRD4, and BRDT. Except for BRDT, which is localized in the testis, the remaining proteins are widely expressed in various tissues. In addition, the BET protein family has been reported to be associated with various diseases including cancer, metabolic diseases and inflammation.

For example, oncogenic fusion of BRD4 or BRD3 and nuclear protein in testis (NUT) genes, which is caused by chromosomal translocations, results in an aggressive cancer termed NUT midline carcinoma (French et al., J Clin Oncol, 22 (2004), 4135-9; French et al., J Clin Pathol, 63 (2008), 492-6). The BRD3/4 bromodomain is conserved in these fusion proteins, and a knockdown or selective BET bromodomain inhibitor, JQ1, causes the death of these cancer cells both in vitro and in animal tumor models (Filippakopoulos et al., Nature, 468 (2010), 1067-73). It is known that JQ1 and other selective BET inhibitors bind to the BET bromodomain and prevent acetyl-lysine binding, which prevents the BET protein from interacting with chromatin, thereby preventing from regulating transcription.

BRD4 has been identified as a target in acute myeloid leukemia (AML) by an RNAi screen (Zuber et al., Nature, 478 (2011), 524-8). These findings were validated in vitro and in vivo using the BET inhibitors JQ1 and I-BET151 (Dawson et al., Nature, 478 (2011), 529-33). In addition, it is known that BET inhibitors have broad anticancer activity in acute leukemia, multiple myeloma and other hematologic malignancies. Acute downregulation of the oncogenic transcription factor Myc upon BET inhibition was observed in several cancer models (Delmore et al., Cell, 146 (2011), 904-17; Mertz et al., Proc Natl Acad Sci US A, 108 (2011), 16669-74). Recent studies suggest that BET inhibitors have broad potential for application in other carcinomas such as lung cancer and brain cancer.

Another BET inhibitor, I-BET762, which is closely related to JQ1 in its chemical structure and BET binding mode, has been reported to regulate the expression of key inflammatory genes in a mouse model and to protect the human body from endotoxin shock and bacteria-induced sepsis (Nicodeme et al., Nature, 468 (2010), 1119-23). In addition, these results have been used to support the clinical evaluation of the BET inhibitor RVX-208 in clinical trials in patients suffering from atherosclerosis, coronary artery disease, dyslipidemia, diabetes mellitus and other cardiovascular diseases (McNeill, Curr Opin Investig Drugs, 3 (2010), 357-64 and www.clinicaltrials.gov).

Both RVX-208 and I-BET762 were found to upregulate apolipoprotein A-I, which is important for reducing cholesterol level in the tissues. In addition, it is believed that the BET protein is related to the proliferation and transcriptional regulation of several viruses, so BET inhibitors may have antiviral activity (Weidner-Glunde, Frontiers in Bioscience 15 (2010), 537-549).

Although several bromodomain inhibitors are known clinically and preclinically, the development of a new bromodomain inhibitor capable of solving the problems of disease recurrence and resistance to therapeutic agents and reducing side effects is urgently required.

On the other hand, redox reactions are present in many physiological processes, and oxygen molecules can produce reactive molecules that are necessary for life but lead to a disease. Other reactive chemical species, including free radicals, also cause pathological conditions. It has been previously known that aerobic metabolism related to tissue damage is caused by reactive oxygen species (ROS). ROS and recently known reactive nitrogen species (RNS), like hormones, are messengers of cell signal transduction, and cause chemical modifications of enzymes and the like and lead to changes in levels of oxidizing agents.

In addition, among 20 essential amino acids, cysteine, methionine, tyrosine and tryptophan are particularly susceptible to oxidation. Therefore, these proteinaceous substances metabolized in the human body cause various modifications such as metal binding, disulfide bond formation, methylation, acetylation, and the like.

Up to now, studies on the signal regulation mechanisms of cells have been focused on phosphorylation, but the present invention has been completed by applying the redox chemistry technology in consideration of the redox control mechanisms such as oxidation and S-nitrosylation depending on the "redox state" for diseases caused by oxidative and nitrification stress. That is, the present inventors have studied and developed a new bromodomain inhibitor in consideration of the redox state, based on the fact that the degree of binding between signaling substances varies depending on the redox state when the BET inhibitor recognizes the lysine residue of the histone protein.

DETAILED DESCRIPTION OF THE INVENTION

Technical Problem

An object of the present invention is to provide a novel quercetin derivative compound having excellent BET protein inhibitory activity.

In addition, another object of the present invention is to provide a pharmaceutical composition for preventing or treating BET protein-related diseases, comprising the compound or pharmaceutically acceptable salt thereof as an active ingredient.

Solution to Problem

According to one aspect of the present invention, there is provided a quercetin derivative compound represented by formula 1 below or a pharmaceutically acceptable salt thereof.

[Formula 1]

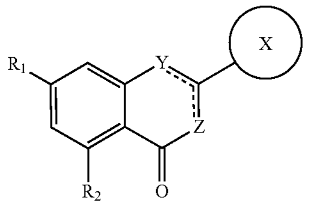

in the formula, ring X is

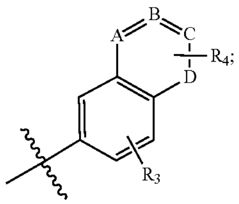

or substituted or unsubstituted aryl, wherein A, B, C, and D are each independently C, C(═O), N, O, S or absent, Y is C, C(═O), N, O or S, Z is $CR_5$ or $NR_5$, --- is each absent or a single bond, $R_1$, $R_2$, and $R_5$ are each independently H, halo, cyano, alkyl, alkenyl, alkynyl, —C(═O)Ra, —C(═O)N(Ra)(Rb), —C(═O)ORa, —N(Ra)(Rb), —N(Ra)C(═O)Rb, —N(Ra)S(═O)Rb, —N(Ra)$S(═O)_2$Rb, —$NO_2$, —ORa, —OC(═O)Ra, —SRa, —S(═O)Ra, —S(═O)N(Ra)(Rb), —$S(═O)_2$Ra, —$S(═O)_2$N(Ra)(Rb), cycloalkyl, heterocycloalkyl, aryl, or heteroaryl, $R_3$ may be the same or different and is at least one selected from the group consisting of H, alkyl, and —ORa, $R_4$ may be the same or different and is at least one selected from the group consisting of H, alkyl, alkenyl, and alkynyl, and Ra and Rb are each independently H, halo, cyano, alkyl, cycloalkyl, or heterocycloalkyl.

According to another aspect of the present invention, there is provided a pharmaceutical composition for preventing or treating BET protein-related diseases, comprising the compound or pharmaceutically acceptable salt thereof as an active ingredient.

The BET protein-related disease may be at least one selected from the group consisting of cancer; autoimmune or inflammatory diseases; metabolic diseases; and viral diseases.

Effects of the Invention

The quercetin derivative compound represented by formula 1 provided in the present invention has excellent inhibitory activity against BET proteins, and thus can be usefully used as an agent for preventing or treating various diseases related to BET.

BEST MODE FOR CARRYING OUT THE INVENTION

Figure 1:
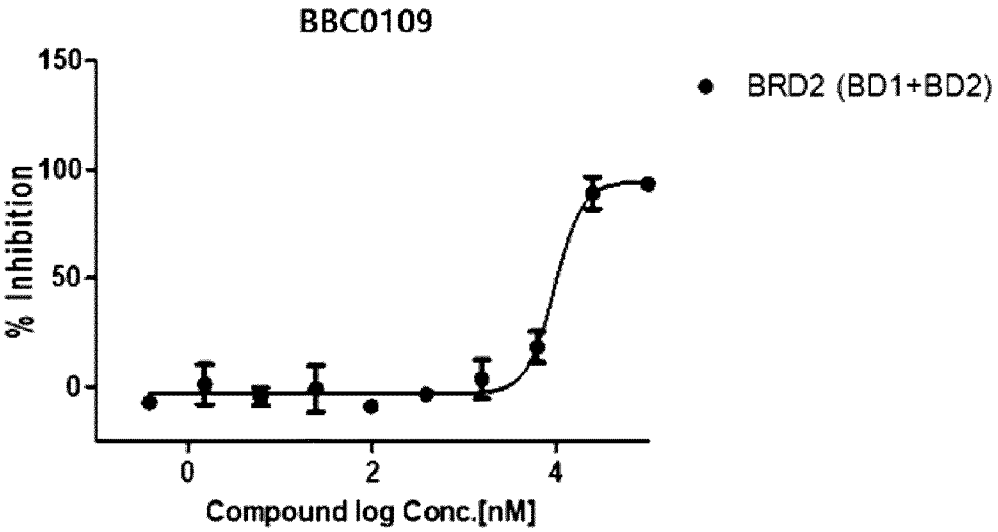
FIG. 1 is a graph showing the inhibitory activity of BRD2 (BD1+BD2) protein binding by Compound 1 of the present invention (BBC0109).

The present invention relates to a novel quercetin derivative compound. More specifically, the present invention relates to a novel quercetin derivative compound having inhibitory activity against BET proteins, and to a pharmaceutical composition for preventing or treating bromodomain extra-terminal (BET) protein-related diseases, comprising the same.

Unless otherwise stated, terms used in the description and claims of the present invention have the meanings to be disclosed below.

In accordance with convention used in the art, in the formula herein,

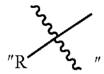

is used to indicate that a moiety or substituent "R" is attached to the backbone structure.

"Alkyl" is a hydrocarbon having primary, secondary, tertiary and/or quaternary carbon atoms, and includes a saturated aliphatic group which may be straight-chain, branched or cyclic, or a combination thereof. For example, an alkyl group may have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Unless otherwise defined, in a preferred embodiment, an alkyl refers to $C_1$-$C_6$ alkyl. Examples of suitable alkyl groups may include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$), but are not limited thereto.

Moreover, as used throughout the specification, examples and claims, the term "alkyl" is intended to include both unsubstituted and substituted alkyl groups, the latter of which refers to an alkyl moiety having a substituent replacing a hydrogen on one or more carbons of the hydrocarbon backbone, which includes a haloalkyl group such as trifluoromethyl, 2,2,2-trifluoroethyl, and the like.

The term "$C_{x-y}$" or "$C_x$-$C_y$," when used in conjunction with a chemical moiety such as acyl, acyloxy, alkyl, alkenyl, alkynyl or alkoxy, is intended to include a group containing from x to y carbons in the chain. $C_0$alkyl represents hydrogen when the group is in the terminal position or a bond when the group is in the internal position. For example, a ($C_1$-$C_6$)alkyl group contains 1 to 6 carbon atoms in the chain.

"Alkoxy" refers to a group having the formula —O-alkyl, wherein the alkyl group as defined above is attached to the parent compound through an oxygen atom. The alkyl moiety of an alkoxy group may have, for example, 1 to 20 carbon atoms (i.e., $C_1$-$C_{20}$ alkoxy), 1 to 12 carbon atoms (i.e., $C_1$-$C_{12}$ alkoxy), 1 to 10 carbon atoms (i.e., $C_1$-$C_{10}$ alkoxy), or 1 to 6 carbon atoms (i.e., $C_1$-$C_6$ alkoxy). Examples of suitable alkoxy groups may include methoxy (—O—$CH_3$ or —OMe), ethoxy (—$OCH_2CH_3$ or -OEt), and t-butoxy (—$OC(CH_3)_3$ or —O-tBu), but are not limited thereto.

"Alkenyl" is a hydrocarbon that has primary, secondary, tertiary and/or quaternary carbon atoms, includes straight-chain, branched and cyclic groups, or a combination thereof, and has at least one unsaturated region, i.e., a carbon-carbon $sp^2$ double bond. For example, an alkenyl group may have 2 to 20 carbon atoms (i.e., $C_2$-$C_{20}$ alkenyl), 2 to 12 carbon atoms (i.e., $C_2$-$C_{12}$ alkenyl), 2 to 10 carbon atoms (i.e., $C_2$-$C_{10}$ alkenyl), or 2 to 6 carbon atoms (i.e., $C_2$-$C_6$ alkenyl). Examples of suitable alkenyl groups may include vinyl (—$CH{=}CH_2$), allyl (—$CH_2CH{=}CH_2$), cyclopentenyl (—$C_5H_7$), and 5-hexenyl (—$CH_2CH_2CH_2CH_2CH{=}CH_2$), but are not limited thereto.

"Alkynyl" is a hydrocarbon that has primary, secondary, tertiary and/or quaternary carbon atoms, includes straight-chain, branched and cyclic groups, or a combination thereof, and has at least one carbon-carbon sp triple bond. For example, an alkynyl group may have 2 to 20 carbon atoms (i.e., $C_2$-$C_{20}$ alkynyl), 2 to 12 carbon atoms (i.e., $C_2$-$C_{12}$ alkynyl), 2 to 10 carbon atoms (i.e., $C_2$-$C_{10}$ alkynyl), or 2 to 6 carbon atoms (i.e., $C_2$-$C_6$ alkynyl). Examples of suitable alkynyl groups may include acetylenic (—$C{\equiv}CH$) and propargyl (—$CH_2C{\equiv}CH$), but are not limited thereto.

As used herein, the term "aryl" includes a substituted or unsubstituted, monovalent or divalent, aromatic hydrocarbon group in which each atom of the ring is carbon and the ring is monocyclic, bicyclic or polycyclic. Preferably, an aryl ring is a 6- to 20-membered ring, a 6- to 14-membered ring, a 6- to 10-membered ring, or more preferably a 6-membered ring. An aryl group may be a polycyclic ring system having two or more cyclic rings in which two or more carbons are common to two adjacent rings, wherein at least one of the rings is aromatic, and for example, the other cyclic rings may be cycloalkyl, cycloalkenyl, cycloalkynyl, aryl, heteroaryl, and/or heterocycloalkyl. An aryl group may include benzene, naphthalene, phenanthrene, anthracene, indene, indane, phenol, aniline, and the like.

As used herein, the term "carbocyclylalkyl," or "cycloalkylalkyl," or "(cycloalkyl)alkyl" refers to an alkyl group substituted with a carbocycle group or a cycloalkyl group.

As used herein, the term "carbocycle," "carbocyclyl," "carbocyclic" or "cycloalkyl" refers to a non-aromatic, saturated or unsaturated, monovalent or divalent ring in which each atom of the ring is carbon and the ring may be monocyclic, bicyclic or polycyclic. A cycloalkyl group may have 3 to 7 carbon atoms as a monocycle, 7 to 12 carbon atoms as a bicycle, and about 20 or less carbon atoms as a polycycle. A monocyclic cycloalkyl has 3 to 7 ring atoms, more typically 5 or 6 ring atoms. A bicyclic cycloalkyl may have 7 to 12 ring atoms and may be a fused ring system, a spirocyclic ring system or a bridged ring system. In exemplary cycloalkyl groups, the atoms may be arranged in a bicyclo[4,5], [5,5], [5,6], or [6,6] system. In a particular embodiment, a cycloalkyl contains 3 to 20 atoms, or 3 to 10 atoms, or more preferably 3 to 7 atoms. Examples of cycloalkyls may include cyclopropyl, cyclobutyl, cyclopentyl, cyclohexyl, cycloheptyl, cyclooctyl, and the like. Unless otherwise specified, a cycloalkyl may be substituted by one or more substituents described herein.

As used herein, the terms "heterocyclylalkyl" and "heterocycloalkyl" refer to an alkyl group substituted with a heterocycloalkyl group.

The terms "heterocyclyl," "heterocycle," "heterocyclic," and "heterocycloalkyl" refer to a substituted or unsubstituted, monovalent or divalent, saturated or partially saturated, non-aromatic ring structure, preferably a 3- to 10-membered ring, more preferably a 3- to 7-membered ring, in which the ring structure comprises at least one heteroatom, preferably 1 to 4 heteroatoms, more preferably 1 to 2 heteroatoms. The terms "heterocyclyl," "heterocycle," "heterocyclic," and "heterocycloalkyl" also include a polycyclic ring system having two or more cyclic rings in which two or more carbons are common to two adjacent rings, wherein at least one of the rings is heterocyclic, and for example, the other cyclic rings may be cycloalkyl, cycloalkenyl, cycloalkynyl, aryl, heteroaryl, and/or heterocyclyl. Bicyclic and polycyclic heterocyclic ring systems may be a fused, bridged, or spiro ring system. A substituted heterocycle includes a heterocyclic ring substituted with any of the substituents disclosed herein, including, for example, a carbonyl group. A heterocyclyl group includes, for example, piperidine, piperazine, pyrrolidine, morpholine, lactone, lactam, and the like. Further exemplary heterocycles may include dihydropyridyl, dihydroindolyl, tetrahydropyridyl (piperidyl), tetrahydrothiophenyl, sulfur-oxidized tetrahydrothiophenyl, indolenyl, piperidinyl, 4-piperidinyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, 6H-1,2,5-thiadiazinyl, 2H,6H-1,5,2-dithiazinyl, pyranyl, chromenyl, xanthenyl, phenoxatinyl, 2H-pyrrolyl, 3H-indolyl, 4H-quinolizinyl, phthalazinyl, naphthyridinyl, quinoxalinyl, quinazolinyl, cinnolinyl, pteridinyl, 4aH-carbazolyl, carbazolyl, O-carbolinyl, phenanthridinyl, acridinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, quinuclidinyl, morpholinyl, and oxazolidinyl (each of which may be substituted or unsubstituted), but are not limited thereto.

"Heteroaryl" refers to a substituted or unsubstituted, monovalent or divalent, aromatic group containing one or more heteroatoms in the ring, which is monocyclic, bicyclic or polycyclic. Non-limiting examples of suitable heteroatoms that may be contained in the aromatic ring may include oxygen, sulfur and nitrogen. In a polycyclic heteroaryl ring system, the ring system has two or more cyclic rings in which two or more carbons are common to two adjacent rings, wherein at least one of the rings is heteroaromatic, and for example, the other cyclic rings may be cycloalkyl, cycloalkenyl, cycloalkynyl, aryl, heteroaryl, and/or heterocyclyl. A heteroaryl group includes, for example, benzofuran, benzothiophene, pyrrole, furan, thiophene, imidazole, indole, isoindole, isoxazole, isothiazole, oxazole, thiazole, quinoline, isoquinoline, pyrazole, pyridine, pyrazine, pyridazine, pyrimidine, and the like (each of which may be substituted or unsubstituted).

The terms "heterocyclyl," "heterocycle," "heterocyclic," and "heterocycloalkyl" refer to a substituted or unsubstituted, monovalent or divalent, saturated or partially saturated, non-aromatic ring structure, preferably a 3- to 10-membered ring, more preferably a 3- to 7-membered ring, in which the ring structure comprises at least one heteroatom, preferably 1 to 4 heteroatoms, more preferably 1 to 2 heteroatoms. The terms "heterocyclyl," "heterocycle," "heterocyclic," and "heterocycloalkyl" also include a polycyclic ring system having two or more cyclic rings in which two or more carbons are common to two adjacent rings, wherein at least one of the rings is heterocyclic, and for example, the other cyclic rings may be cycloalkyl, cycloalkenyl, cycloalkynyl, aryl, heteroaryl, and/or heterocyclyl. Bicyclic and polycyclic heterocyclic ring systems may be a fused, bridged, or spiro ring system. A substituted heterocycle includes a heterocyclic ring substituted with any of the substituents disclosed herein, including, for example, a carbonyl group. A heterocyclyl group includes, for example, piperidine, piperazine, pyrrolidine, morpholine, lactone, lactam, and the like. Further exemplary heterocycles may include dihydropyridyl, dihydroindolyl, tetrahydropyridyl (piperidyl), tetrahydrothiophenyl, sulfur-oxidized tetrahydrothiophenyl, indolenyl, piperidinyl, 4-piperidinyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, 6H-1,2,5-thiadiazinyl, 2H,6H-1,5,2-dithiazinyl, pyranyl, chromenyl, xanthenyl, phenoxatinyl, 2H-pyrrolyl, 3H-indolyl, 4H-quinolizinyl, phthalazinyl, naphthyridinyl, quinoxalinyl, quinazolinyl, cinnolinyl, pteridinyl, 4aH-carbazolyl, carbazolyl, O-carbolinyl, phenanthridinyl, acridinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, quinuclidinyl, morpholinyl, and oxazolidinyl (each of which may be substituted or unsubstituted), but are not limited thereto.

As used herein, the terms "halo" and "halogen" refer to a halogen and include chloro, fluoro, bromo, and iodo.

"Amino" refers to the group —$NH_2$.

"Cyano" refers to the group —CN.

"Nitro" refers to the group —$NO_2$.

"Carboxy" refers to the group —C(O)OH.

"Aldehyde" refers to the group —CHO.

"Alkoxycarbonyl" refers to the group —C(O)O(alkyl) or —C(O)O(cycloalkyl), wherein the alkyl and cycloalkyl are as defined above.

"Acyl halide" refers to a compound comprising the group —C(O)-halogen.

The present invention relates to a compound represented by formula 1 below or a pharmaceutically acceptable salt thereof.

[Formula 1]

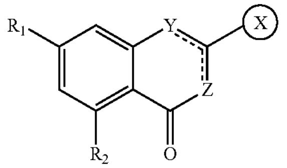

in the formula, ring X is

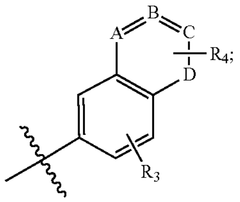

or substituted or unsubstituted aryl, wherein A, B, C, and D are each independently C, C(═O), N, O, S or absent, Y is C, C(═O), N, O or S, Z is $CR_5$ or $NR_5$, ---- is each absent or a single bond, $R_1$, $R_2$, and $R_5$ are each independently H, halo, cyano, alkyl, alkenyl, alkynyl, —C(═O)Ra, —C(═O)N(Ra)(Rb), —C(═O)ORa, —N(Ra)(Rb), —N(Ra)C(═O)Rb, —N(Ra)S(═O)Rb, —N(Ra)S(═O)$_2$Rb, —$NO_2$, —ORa, —OC(═O)Ra, —SRa, —S(═O)Ra, —S(═O)N(Ra)(Rb), —S(═O)$_2$Ra, —S(═O)$_2$N(Ra)(Rb), cycloalkyl, heterocycloalkyl, aryl, or heteroaryl, $R_3$ may be the same or different and is at least one selected from the group consisting of H, alkyl, and —ORa, $R_4$ may be the same or different and is at least one selected from the group consisting of H, alkyl, alkenyl, and alkynyl, and Ra and Rb are each independently H, halo, cyano, alkyl, cycloalkyl, or heterocycloalkyl.

In one embodiment, in the compound of formula 1, the ring X may be

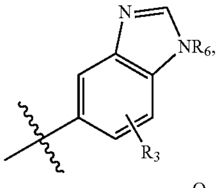

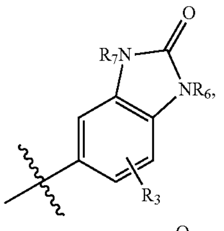

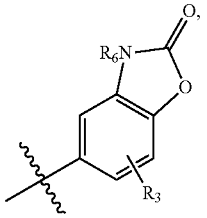

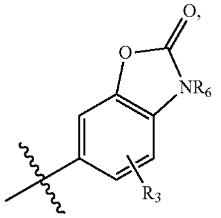

-continued

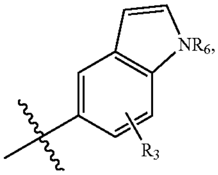
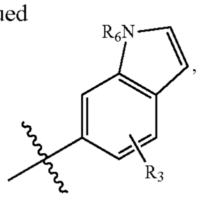
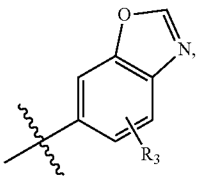
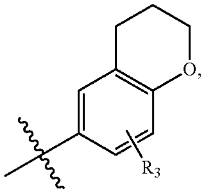
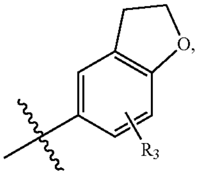
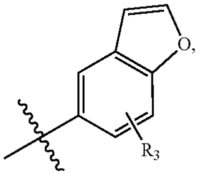
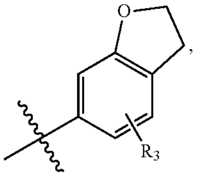
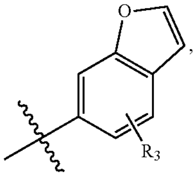

or

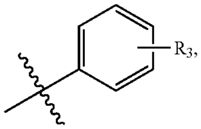

$R_3$ may be the same or different and may be at least one selected from the group consisting of H, $C_1$-$C_6$alkyl, and —ORa, wherein Ra may be H, $C_1$-$C_6$alkyl, cycloalkyl, or a 3- to 10-membered heterocycloalkyl comprising a heteroatom selected from N, O, or S, and $R_6$ and $R_7$ may be each independently H or $C_1$-$C_6$alkyl.

In one embodiment, in the compound of formula 1,

Y may be N or O,

Z may be $CR_5$ or $NR_5$, and $R_1$, $R_2$ and $R_5$ may be each independently H, $C_1$-$C_6$alkyl, OH, or —O—$C_1$-$C_6$alkyl.

In one embodiment, in the compound of formula 1, the ring X may be

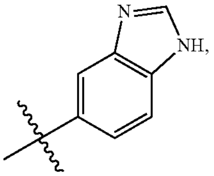
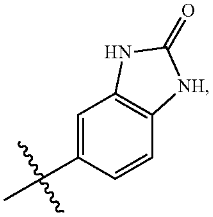
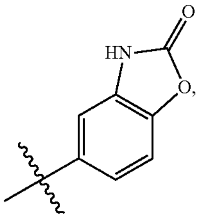
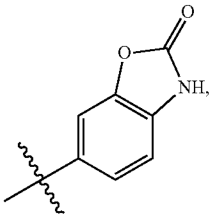

-continued

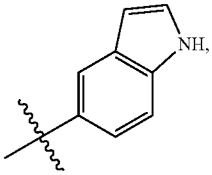
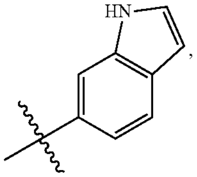
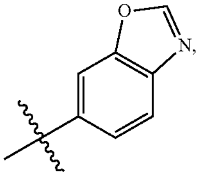
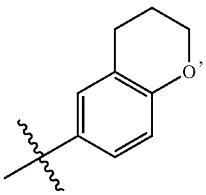
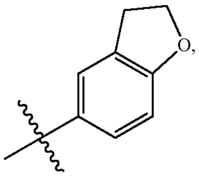
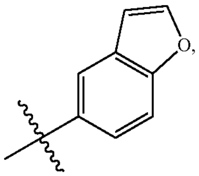
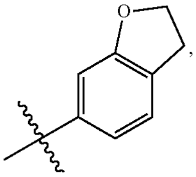
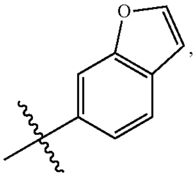
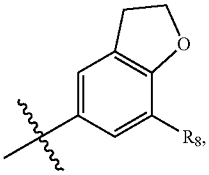
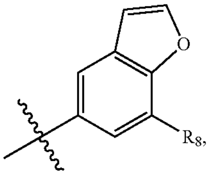

or

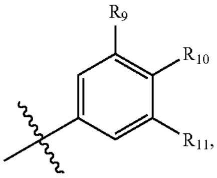

$R_8$ may be H or $C_1$-$C_6$alkyl, and $R_9$, $R_{10}$ or $R_{11}$ may be each independently H, $C_1$-$C_6$alkyl, or —ORa, wherein Ra may be H, $C_1$-$C_6$alkyl, or a 3- to 10-membered heterocycloalkyl comprising a heteroatom of O.

Preferred examples according to the present invention are as follows, but are not limited thereto.

| No. | Compound | Structure |
|---|---|---|
| 1 | BBC0109 | 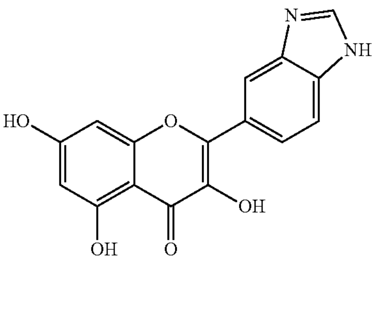 [SMILES: O=c1c(O)c(-c2ccc3[nH]cnc3c2)oc2cc(O)cc(O)c12] |

-continued
| No. | Compound | Structure |
|---|---|---|
| 2 | BBC0110 | 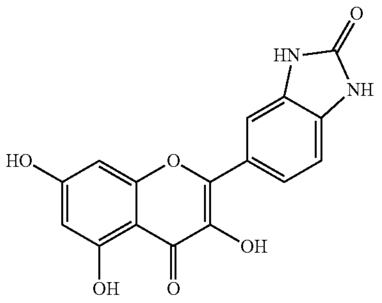 [SMILES: O=c1[nH]c2ccc(-c3oc4cc(O)cc(O)c4c(=O)c3O)cc2[nH]1] |
| 3 | BBC0111 | 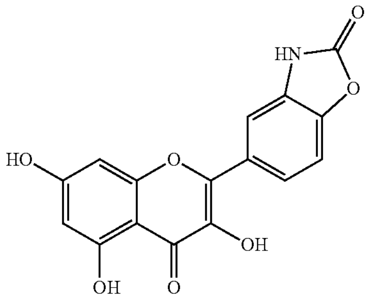 [SMILES: O=c1[nH]c2cc(-c3oc4cc(O)cc(O)c4c(=O)c3O)ccc2o1] |
| 4 | BBC0113 | 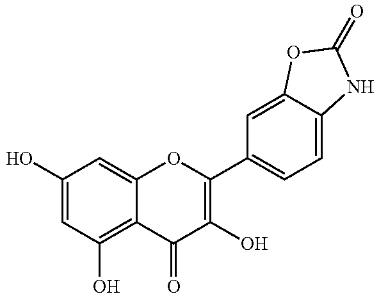 [SMILES: O=c1[nH]c2ccc(-c3oc4cc(O)cc(O)c4c(=O)c3O)cc2o1] |
| 5 | BBC0114 | 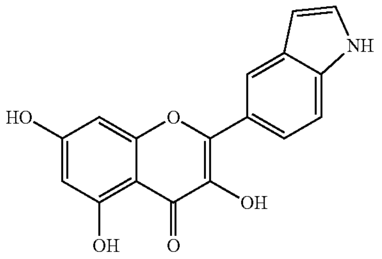 [SMILES: O=c1c(O)c(-c2ccc3[nH]ccc3c2)oc2cc(O)cc(O)c12] |
| 6 | BBC0115 | 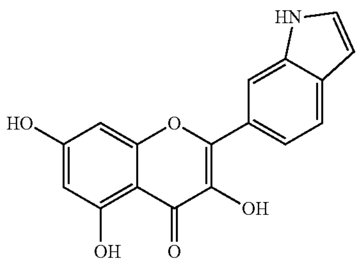 [SMILES: O=c1c(O)c(-c2ccc3cc[nH]c3c2)oc2cc(O)cc(O)c12] |
-continued
| No. | Compound | Structure |
|---|---|---|
| 7 | BBC0116 | 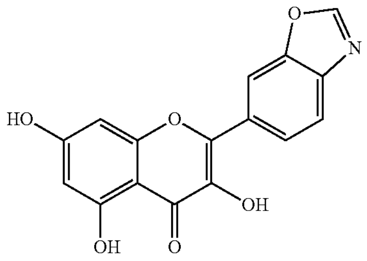 [SMILES: O=c1c(O)c(-c2ccc3ncoc3c2)oc2cc(O)cc(O)c12] |
| 8 | BBC0309 | 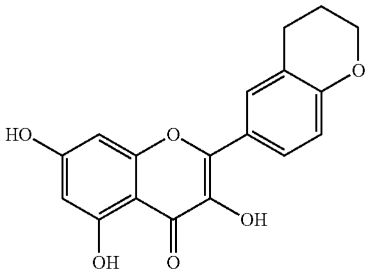 [SMILES: O=c1c(O)c(-c2ccc3c(c2)CCCO3)oc2cc(O)cc(O)c12] |
| 9 | BBC0310 | 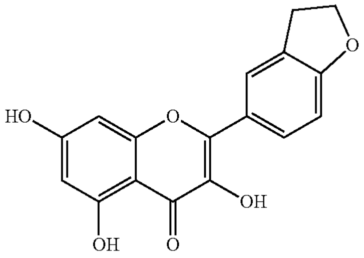 [SMILES: O=c1c(O)c(-c2ccc3c(c2)CCO3)oc2cc(O)cc(O)c12] |
| 10 | BBC0311 | 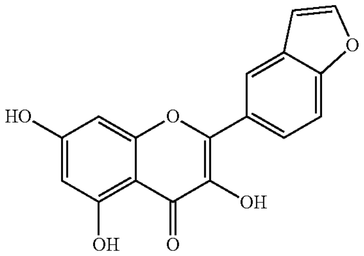 [SMILES: O=c1c(O)c(-c2ccc3occc3c2)oc2cc(O)cc(O)c12] |
| 11 | BBC0312 | 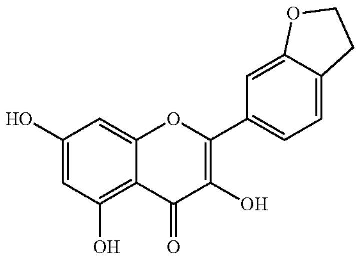 [SMILES: O=c1c(O)c(-c2ccc3c(c2)OCC3)oc2cc(O)cc(O)c12] |
| 12 | BBC0313 | 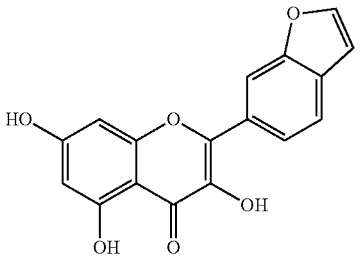 [SMILES: O=c1c(O)c(-c2ccc3ccoc3c2)oc2cc(O)cc(O)c12] |

-continued

| No. | Compound | Structure |
|---|---|---|
| 13 | BBC0406 | 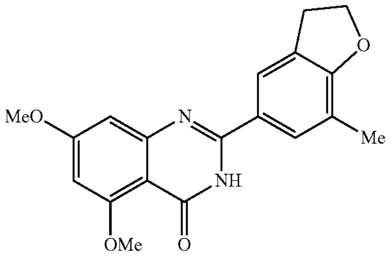 [SMILES: COc1cc(OC)c2c(=O)[nH]c(-c3cc(C)c4c(c3)CCO4)nc2c1] |
| 14 | BBC0407 | 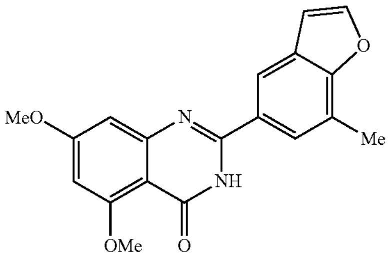 [SMILES: COc1cc(OC)c2c(=O)[nH]c(-c3cc(C)c4occc4c3)nc2c1] |
| 15 | BBC0301 | 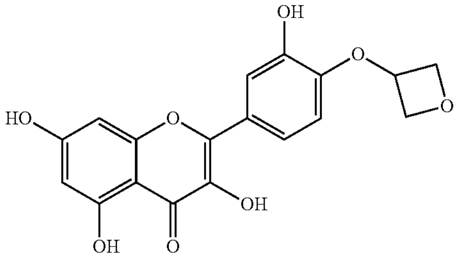 [SMILES: O=c1c(O)c(-c2ccc(OC3COC3)c(O)c2)oc2cc(O)cc(O)c12] |
| 16 | BBC0302 | 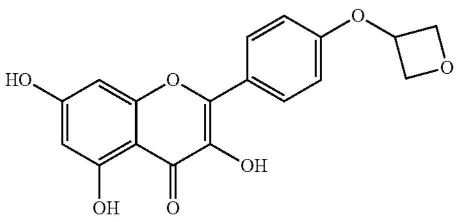 [SMILES: O=c1c(O)c(-c2ccc(OC3COC3)cc2)oc2cc(O)cc(O)c12] |
| 17 | BBC0303 | 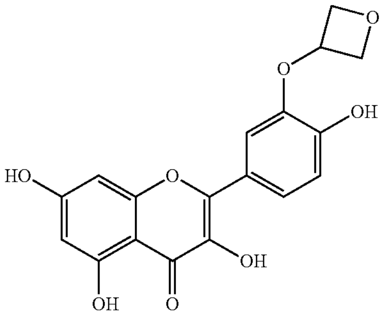 [SMILES: O=c1c(O)c(-c2ccc(O)c(OC3COC3)c2)oc2cc(O)cc(O)c12] |

-continued

| No. | Compound | Structure |
|---|---|---|
| 18 | BBC0305 | 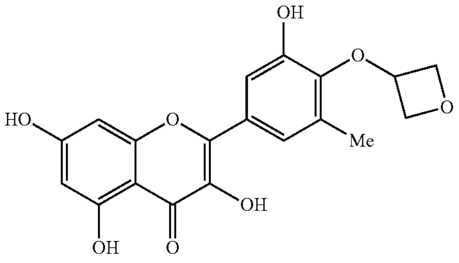 [SMILES: Cc1cc(-c2oc3cc(O)cc(O)c3c(=O)c2O)cc(O)c1OC1COC1] |
| 19 | BBC0306 | 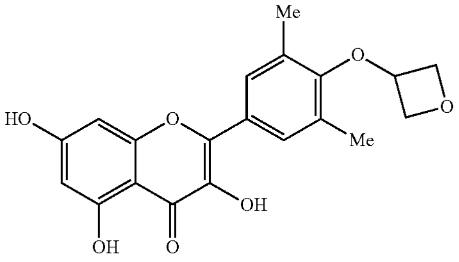 [SMILES: Cc1cc(-c2oc3cc(O)cc(O)c3c(=O)c2O)cc(C)c1OC1COC1] |
| 20 | BBC0307 | 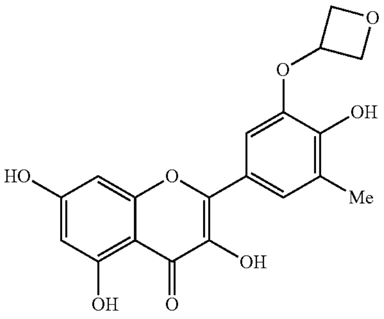 [SMILES: Cc1cc(-c2oc3cc(O)cc(O)c3c(=O)c2O)cc(OC2COC2)c1O] |
| 21 | BBC0104 | 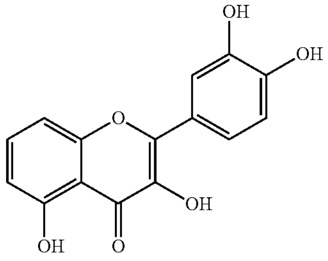 [SMILES: O=c1c(O)c(-c2ccc(O)c(O)c2)oc2cccc(O)c12] |
| 22 | BBC0105 | 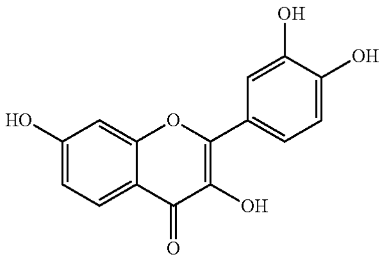 |

The compound according to the present invention are capable of forming a pharmaceutically acceptable salt. The pharmaceutically acceptable salt is not particularly limited as long as it is an acid that forms a non-toxic acid addition salt containing a pharmaceutically acceptable anion. The pharmaceutically acceptable salt may include, for example, acid addition salts formed by inorganic acids such as hydrochloric acid, sulfuric acid, nitric acid, phosphoric acid, hydrobromic acid, hydroiodic acid, and the like; organic acids such as tartaric acid, formic acid, citric acid, acetic acid, trichloroacetic acid, trifluoroacetic acid, gluconic acid, benzoic acid, lactic acid, fumaric acid, maleic acid, and the like; and sulfonic acids such as methanesulfonic acid, benzenesulfonic acid, p-toluenesulfonic acid, naphthalenesulfonic acid, and the like.

In another aspect, the present invention provides a pharmaceutical composition for preventing or treating bromodomain extra-terminal (BET) protein-related diseases, containing the compound represented by formula 1 or pharmaceutically acceptable salt thereof as an active ingredient.

The pharmaceutical composition of the present invention is useful for preventing or treating various diseases related to BET proteins because the compound represented by formula 1 contained therein inhibits the BET proteins. The BET protein-related disease may be cancer; autoimmune or inflammatory diseases; metabolic diseases; or viral diseases.

In one embodiment of the present invention, the cancer may be at least one selected from the group consisting of hematologic cancer, multiple myeloma, acute myeloid leukemia, malignant lymphoma, aplastic anemia, thymus cancer, ovarian cancer, cervical cancer, breast cancer, colorectal cancer, liver cancer, stomach cancer, pancreatic cancer, colon cancer, peritoneal metastatic cancer, skin cancer, bladder cancer, prostate cancer, thyroid cancer, lung cancer, osteosarcoma, fibrous tumor, and brain tumor, but is not limited thereto.

In one embodiment of the present invention, the autoimmune or inflammatory disease may be at least one selected from the group consisting of rheumatoid arthritis, systemic lupus erythematosus, multiple sclerosis, type 1 diabetes mellitus, hyperthyroidism, myasthenia, Crohn's disease, ankylosing spondylitis, psoriasis, autoimmune pernicious anemia and Sjogren's syndrome, allergy, allergic rhinitis, arthritis, asthma, chronic obstructive pulmonary disease, degenerative joint disease, dermatitis, organ rejection, eczema, hepatitis, inflammatory bowel disease, sepsis, sepsis syndrome, septic shock, and nonalcoholic steatohepatitis, but is not limited thereto.

In one embodiment of the present invention, the metabolic disease may be at least one selected from the group consisting of hypertriglyceridemia, obesity, hyperlipidemia, hyperinsulinemia, hyperglycemia, arteriosclerosis, hypertension, type 2 diabetes mellitus, and insulin resistance disease, but is not limited thereto.

In one embodiment of the present invention, the viral disease may be at least one selected from the group consisting of infantile paralysis, acute hemorrhagic conjunctivitis, viral meningitis, hand foot and mouth disease, hepatitis, myositis, myocarditis, pancreatitis, epidemic myalgia, encephalitis, common cold, herpangina, foot and mouth disease, asthma, bronchiolitis, bronchitis, chronic obstructive pulmonary disease, pneumonia, sinusitis, otitis media, herpes simplex, herpes zoster, stomatitis, and chickenpox, but is not limited thereto.

According to another embodiment of the present invention, there is provided a pharmaceutical formulation comprising the pharmaceutical composition.

The pharmaceutical formulation of the present invention may be in various oral dosage forms such as tablets, pills, powders, capsules, syrups or emulsions, or parenteral dosage forms such as injections, for example, injections for intramuscular, intravenous or subcutaneous administration.

In addition, the pharmaceutical formulation may be formulated according to a conventional method by adding conventional non-toxic pharmaceutically acceptable additives, which are one or more selected from the group consisting of carriers, additives, and excipients as a specific example, in addition to the active ingredient.

Hereinafter, the present invention will be described in detail by the following examples and experimental examples. However, the following examples and experimental examples are only for illustrating the present invention and the content of the present invention is not limited by the following examples and experimental examples.

EXAMPLE

The structure of the compound was confirmed by nuclear magnetic resonance (NMR) and mass spectrometry (MS). NMR was measured with a Bruker Avance-400 or Bruker Avance 300 instrument. The solvents for the measurement were deuterium substituted-dimethyl sulfoxide (DMSO-d6), deuterium substituted-chloroform ($CDCl_3$) and deuterium substituted-methanol ($CD_3OD$), and the internal standard was tetramethylsilane (TMS).

High performance liquid chromatography (HPLC) was performed by flash chromatography or column chromatography.

Thin layer chromatography (TLC) was performed on a silica gel plate. 1000 mesh silica gel was used for thin layer chromatography. In addition, the dimension of the silica gel plate used for TLC was 20 to 25 μm, and the dimension of the silica gel plate used for product purification was 40 to 45 μm.

Ultraviolet light, iodine, and potassium permanganate were used in water for visualization.

The known starting materials of the present invention may be prepared by conventional synthetic methods in the art, or may be purchased from Alfa Aesar, Aldrich, and the like.

Example 1: Synthesis of Compound 1 (BBC0109)

[Reaction Scheme]

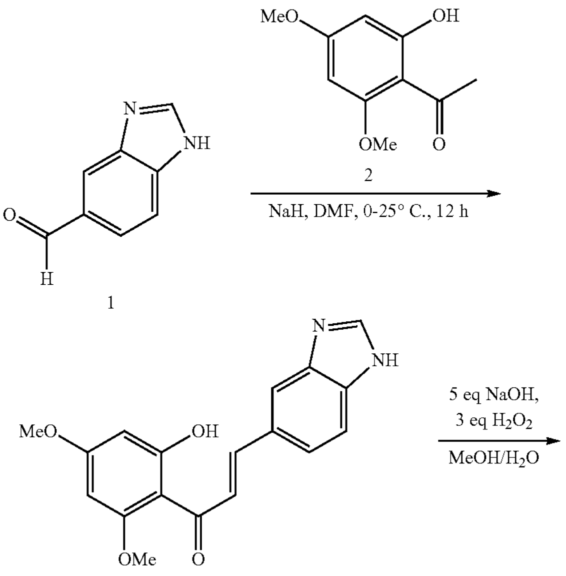

1 2 3

-continued

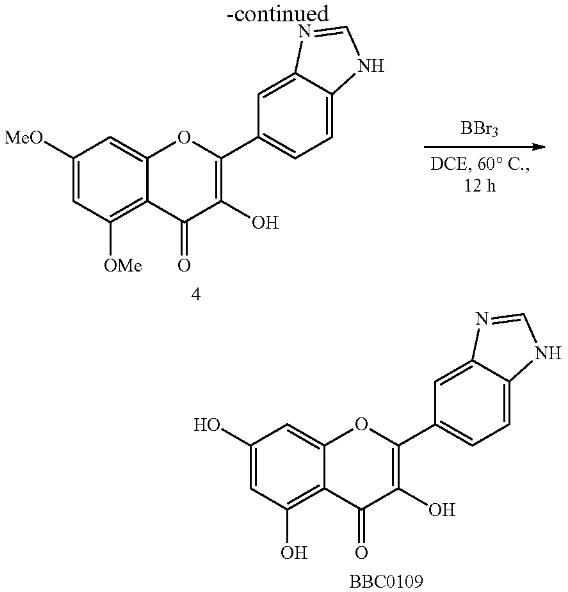

4

BBC0109

Step 1. Preparation of 3-(1H-benzodiimidazol-5-yl)-1-(2-hydroxy-4,6-dimethoxyphenyl)prop-2-en-1-one

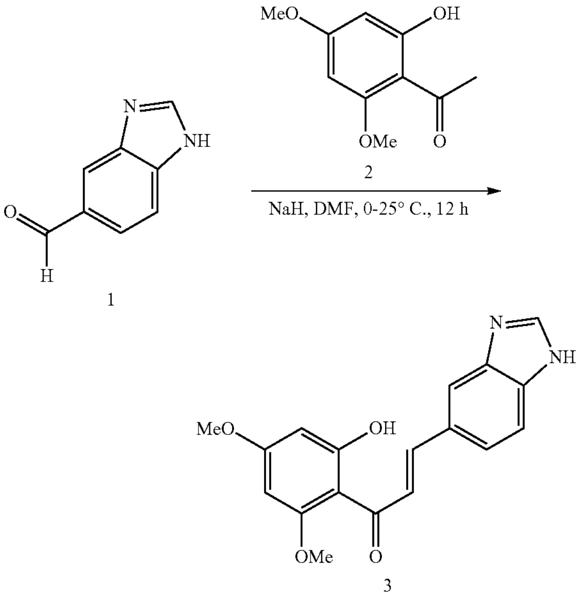

2

1

3

1-(2-hydroxy-4,6-dimethoxyphenylketene (500 mg, 2.55 mmol, 1 eq) was dissolved in DMF (15 mL), and then sodium hydroxide (254.84 mg, 6.37 mmol, 60% purity, 2.5 eq) and 1H-benzodiimidazole-5-carbaldehyde (409.69 mg, 2.80 mmol, 1.1 eq) were added at 0° C., and the mixture was stirred at 25° C. for 12 hours. After the reaction was completed, it was extracted with distilled water and ethyl acetate. The organic layer was dried over anhydrous sodium sulfate, concentrated, and then purified by column chromatography to obtain Intermediate 3 (300 mg, 924.98 umol, 36.30% yield).

LCMS: RT=0.821 min, m/z: 325.2 (M+H)+

Step 2. Synthesis of 2-(1H-benzoimidazol-5-yl)-3-hydroxy-5,7-dimethoxy-4H-chromen-4-one

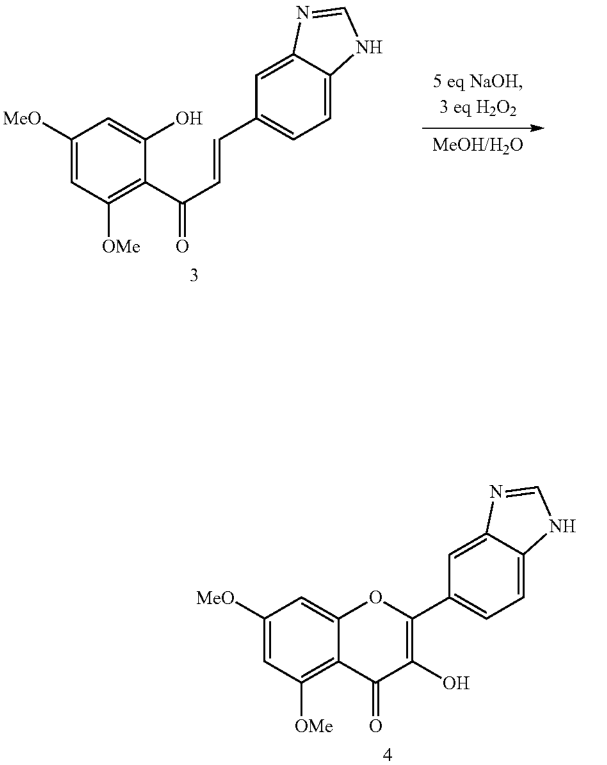

3

4

3-(1H-benzodiimidazol-5-yl)-1-(2-hydroxy-4,6-dimethoxyphenyl)prop-2-en-1-one (270 mg, 832.49 umol, 1 eq) was dissolved in methanol (60 mg)/water (30 mL), and then sodium hydroxide (170.09 mg, 4.25 mmol, 5.11 eq) and hydrogen peroxide (288.00 mg, 2.54 mmol, 244.07 uL, 30% purity, 3.05 eq) were added at 0° C., and the mixture was stirred at 25° C. for 12 hours. After the reaction was completed, it was diluted with distilled water, adjusted to pH 5, and then extracted with ethyl acetate. The organic layer was dried over anhydrous sodium sulfate and concentrated to obtain Intermediate 4 (120 mg).

LCMS: RT=0.650 min, m/z: 339.0 (M+H)+

Step 3. Preparation of 2-(1H-benzodiimidazol-5-yl)-3,5,7-trihydroxy-4H-chromen-4-one (BBC0109)

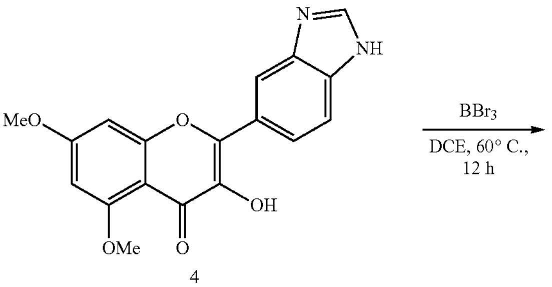

4

-continued

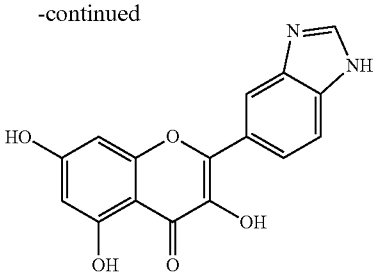

BBC0109

2-(1H-benzoimidazol-5-yl)-3-hydroxy-5,7-dimethoxy-4H-chromen-4-one (50 mg, 147.79 umol, 1 eq) was dissolved in dichloroethane (3 mL), and then boron tribromide (370.25 mg, 1.48 mmol, 142.40 uL, 10 eq) was added thereto, and then stirred at 60° C. for 12 hours. After the reaction was completed, methanol was added, concentrated, and then purified by prep-HPLC to obtain Compound 1 (3.23 mg, 9.67 umol, 3.27% yield, 92.9% purity).

$^1$H NMR (400 MHz, METHANOL-d4) δ ppm 8.60 (1H, s), 8.33 (1H, s), 8.15-8.22 (1H, m), 7.77 (1H, d, J=8.4 Hz), 6.49 (1H, d, J=2.0 Hz), 6.24 (1H, d, J=2.0 Hz)

LCMS: RT=2.049 min, m/z: 311.0 (M+H)+

Example 2: Synthesis of Compound 2 (BBC0110)

[Reaction Scheme]

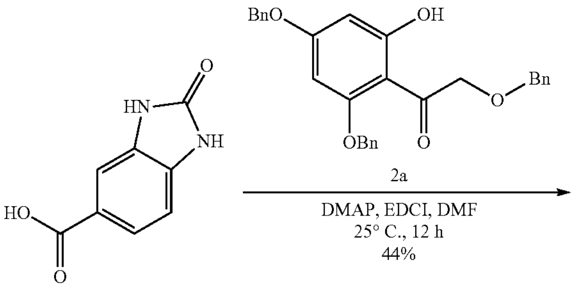

1

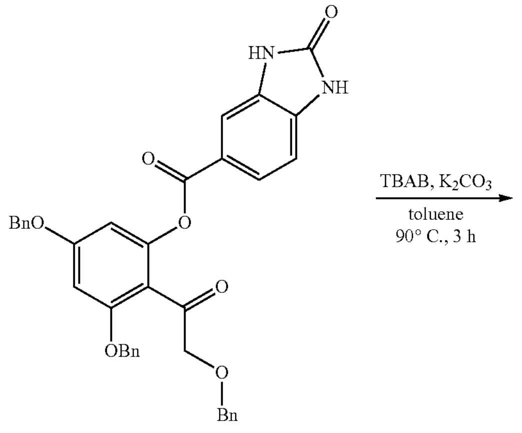

2

-continued

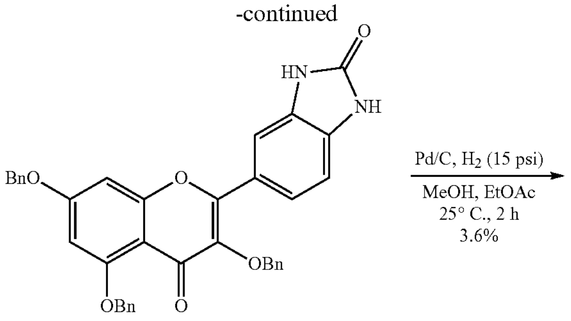

3

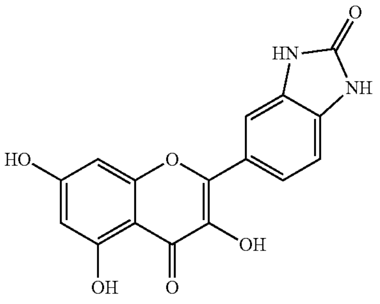

BBC0110

5-(3,5,7-trihydroxy-4-oxo-chromen-2-yl)-1,3-dihydrobenzimidazol-2-one (BBC0110) (2.64 mg, 7.3 umol, 3.6% yield, 90.5% purity) was obtained from 2-oxo-1,3-dihydrobenzimidazole-5-carboxylic acid 1 (196.0 mg, 1.1 mmol, 2.0 eq) by the above reaction scheme.

LCMS: RT=2.270 min, m/z: 327.0 (M+H)+

$^1$HNMR (400 MHz, DMSO-d6) δ ppm 10.71-10.88 (1H, m) 7.78-7.87 (2H, m) 7.08 (1H, d, J=8.4 Hz) 6.39 (1H, d, J=1.6 Hz) 6.15 (1H, d, J=2.0 Hz).

Example 3: Synthesis of Compound 3 (BBC0111)

[Reaction Scheme 1]

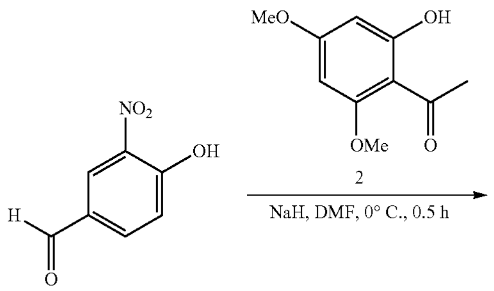

1

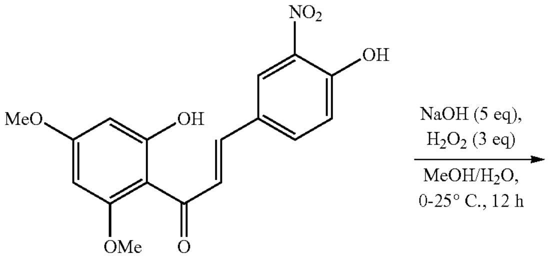

3

-continued
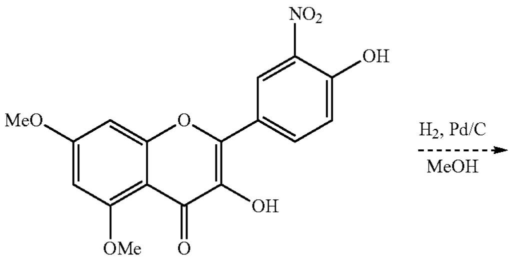
4
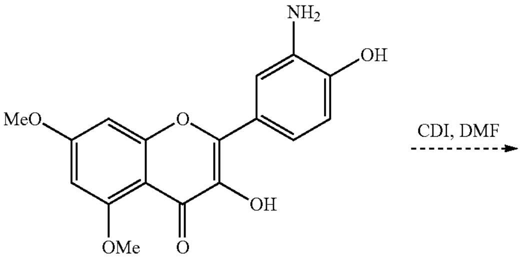
5
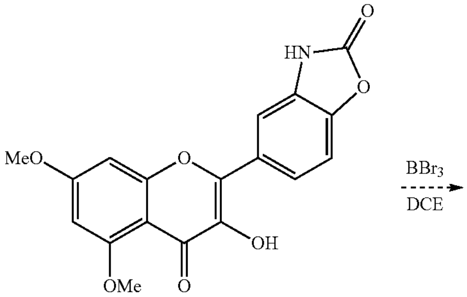
6
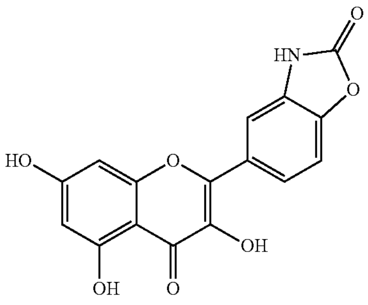
BC0111
[Reaction Scheme 2]
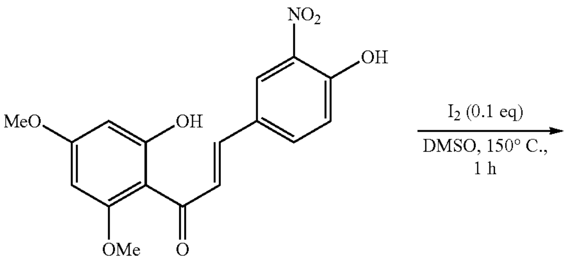
3
-continued
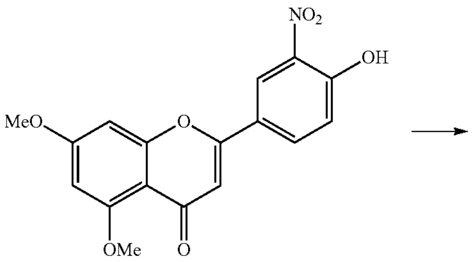
7
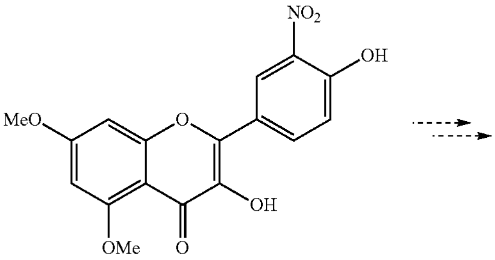
4
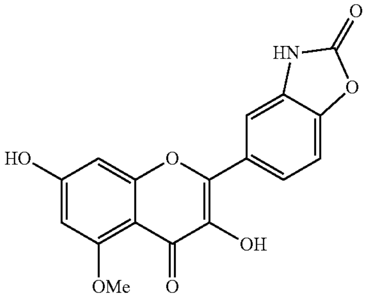
BBC0111
[Reaction Scheme 3]
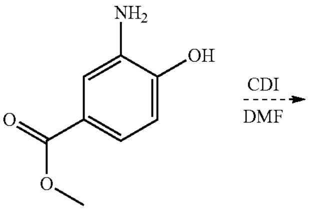
1
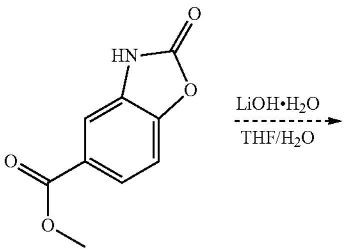
2

-continued
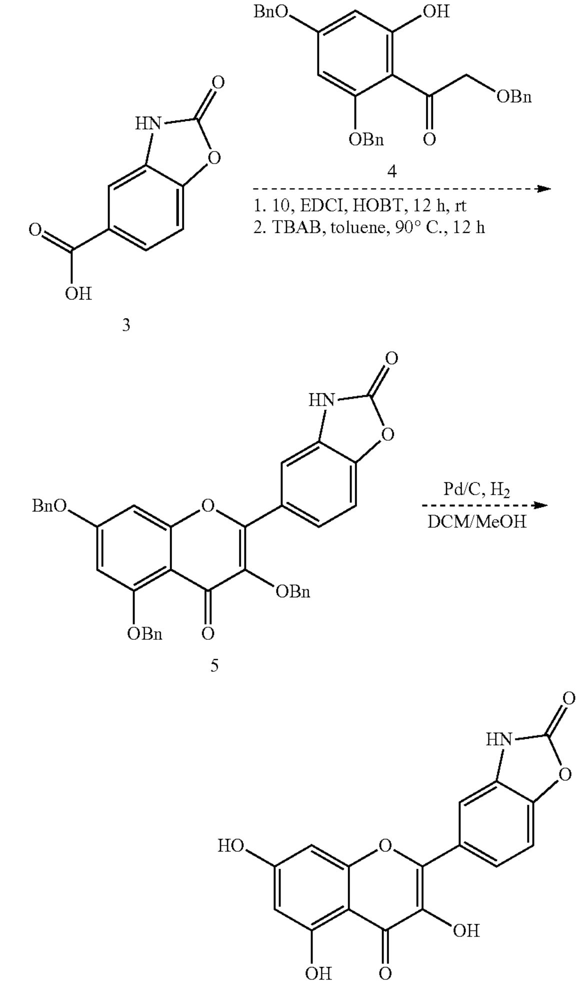
4, 3, 5, BBC0111
The compound of BBC0111 was prepared by any one of Reaction Schemes 1 to 3 above.
Example 4: Synthesis of Compound 4 (BBC0113)
[Reaction Scheme]
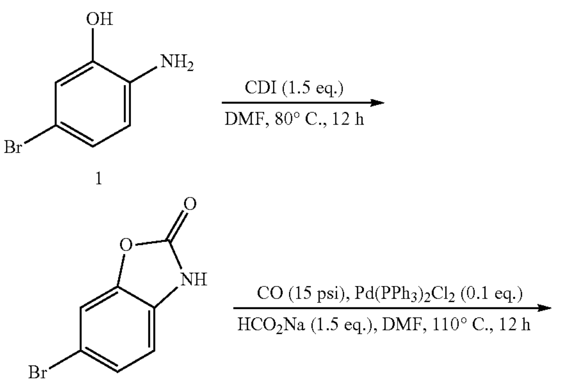
1, 2
-continued
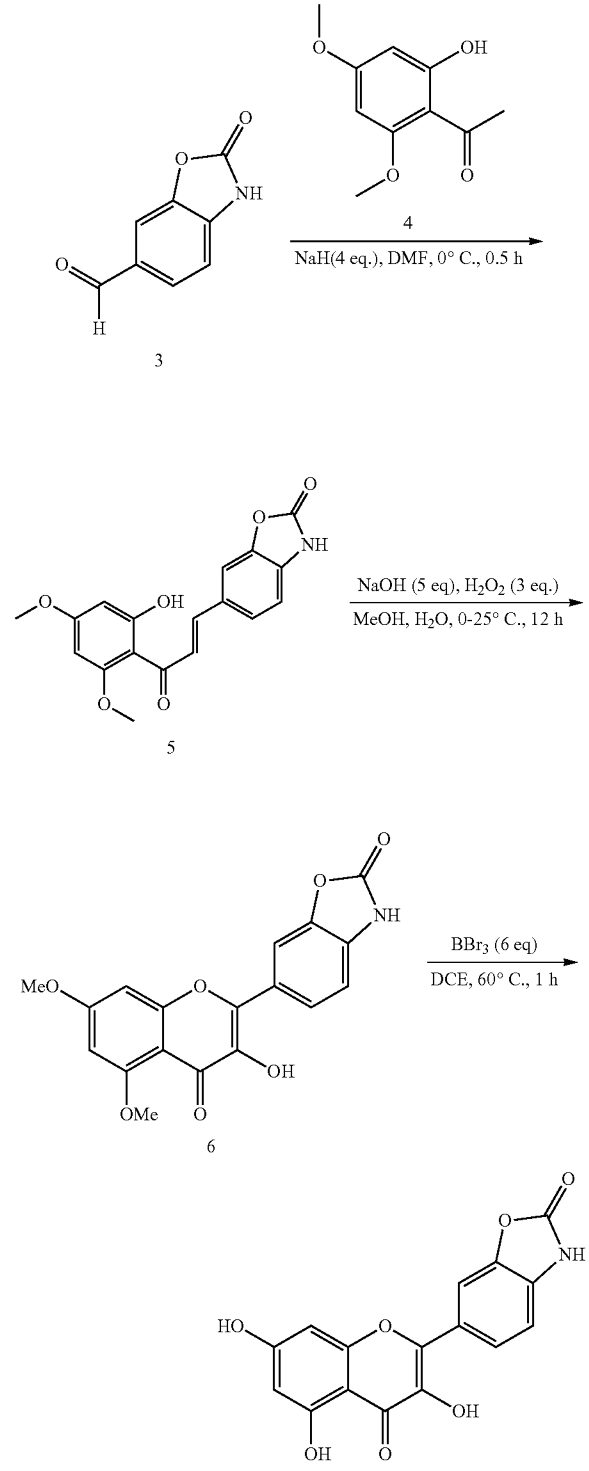
3, 4, 5, 6, BBC0113
6-(3,5,7-trihydroxy-4-oxo-chromen-2-yl)-3H-1,3-benzoxazol-2-one (BBC0113) (4.6 mg, 12.8 umol, 18.2% yield, 91% purity) was obtained from 2-amino-5-bromo-phenol 1 (1.0 g, 5.32 mmol, 1.0 eq).
LCMS: RT=2.447 min, m/z: 328.0 (M+H)+
$^1H$ NMR (400 MHz, MeOD) δ ppm 8.11 (2H, s), 7.22 (1H, br d, J=8.0 Hz), 6.44 (1H, s), 6.20 (1H, s)

Example 5: Synthesis of Compound 5 (BBC0114)

[Reaction Scheme]

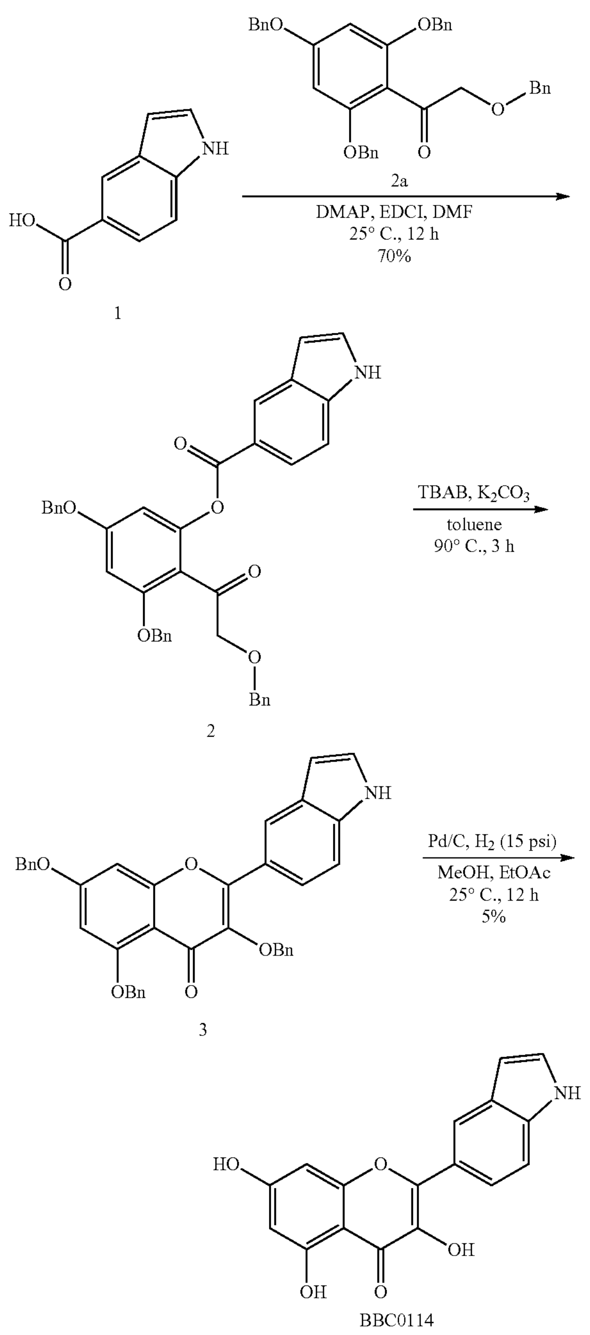

3,5,7-trihydroxy-2-(1H-indol-5-yl)chromen-4-one (BBC0114) (2.38 mg, 7.16 umol, 4.6% yield, 93% purity) was obtained from 1H-indole-5-carboxylic acid 1 (92.2 mg, 572.0 umol, 2.0 eq).

LCMS: RT=2.666 min, m/z: 310.0 (M+H)+

$^1$H NMR (400 MHz, MeOD) δ ppm 8.50 (1H, d, J=1.2 Hz) 7.99 (1H, dd, J=8.8, 1.6 Hz) 7.50 (1H, d, J=8.8 Hz) 7.32 (1H, d, J=3.2 Hz) 6.58 (1H, dd, J=3.2, 0.8 Hz) 6.45 (1H, d, J=2.0 Hz) 6.20 (1H, d, J=2.0 Hz)

Example 6: Synthesis of Compound 6 (BBC0115)

[Reaction Scheme]

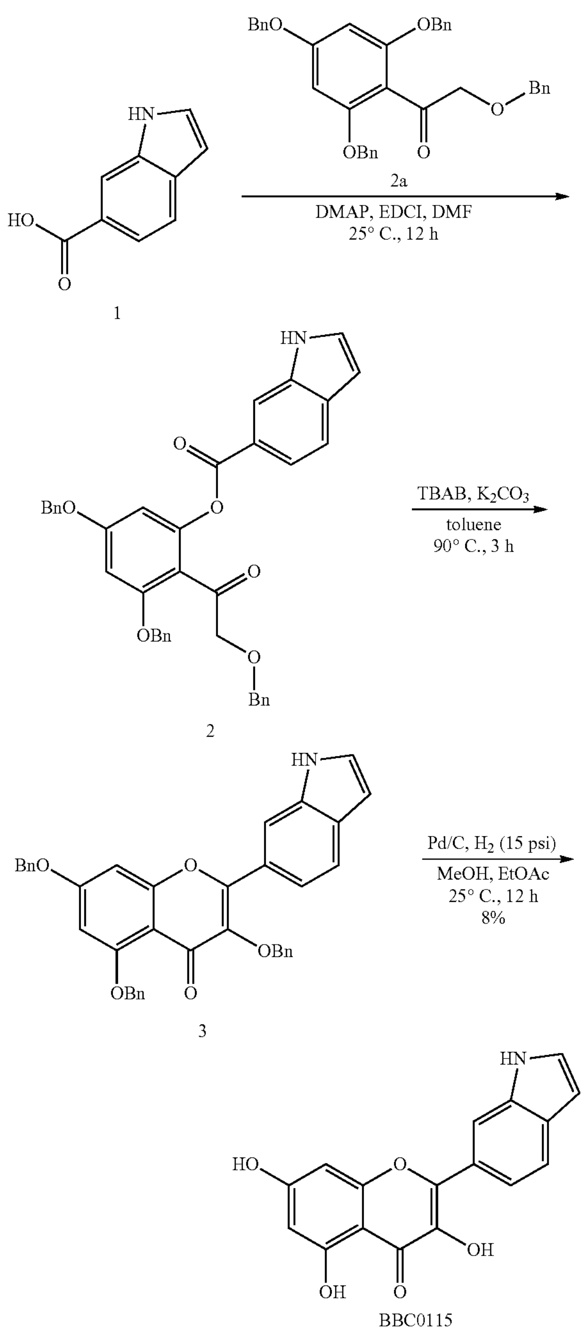

3,5,7-trihydroxy-2-(1H-indol-6-yl)chromen-4-one (BBC0115) (4.73 mg, 13.8 umol, 8.0% yield, 90.4% purity) was obtained from 1H-indole-6-carboxylic acid 1 (106.4 mg, 660.1 umol, 2.0 eq).

LCMS: RT=2.711 min, m/z: 310.0 (M+H)+

$^1$H NMR (400 MHz, DMSO-d6) δ ppm 12.52 (1H, s) 11.45 (1H, br s) 10.81 (1H, s) 9.48 (1H, s) 8.39 (1H, s) 7.82 (1H, dd, J=8.4, 1.6 Hz) 7.69 (1H, d, J=8.4 Hz) 7.54 (1H, t, J=2.8 Hz) 6.45-6.54 (2H, m) 6.21 (1H, d, J=2.0 Hz)

Example 7: Synthesis of Compound 7 (BBC0116)
[Reaction Scheme 1]
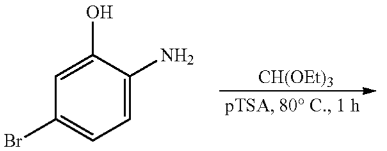
1
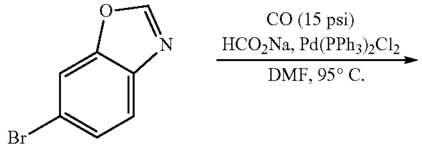
2
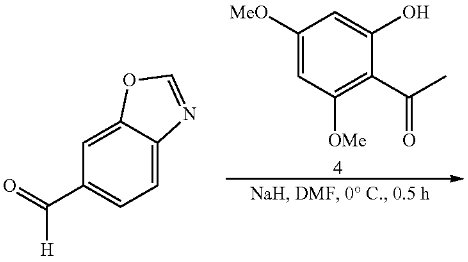
3
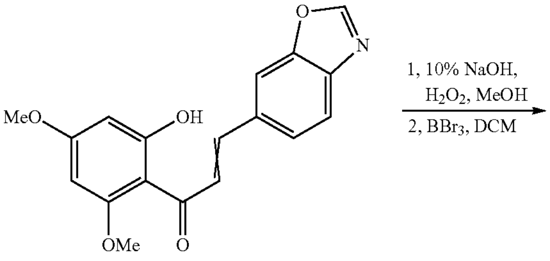
5
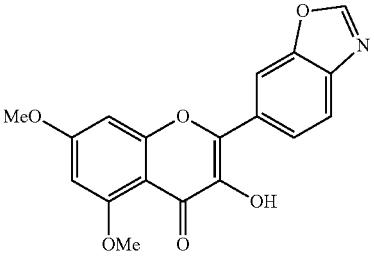
BBC0116
[Reaction Scheme 2]
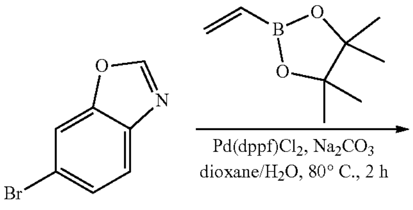
6
-continued
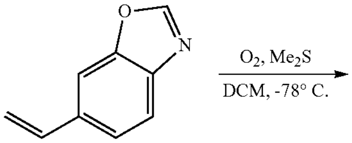
7
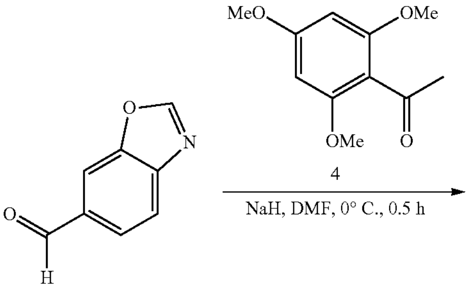
8
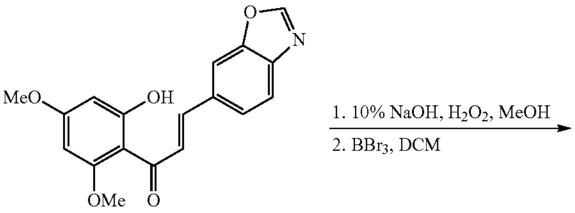
9
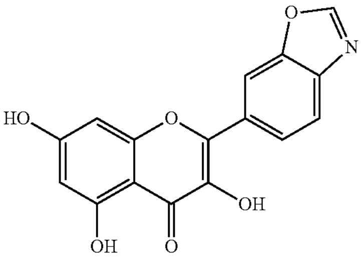
BBC0116
[Reaction Scheme 3]
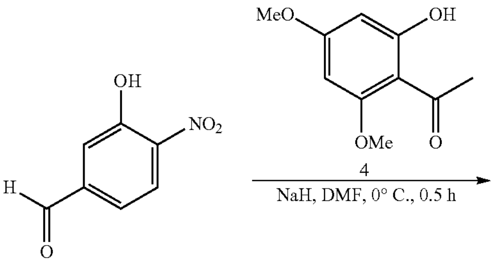
1

-continued
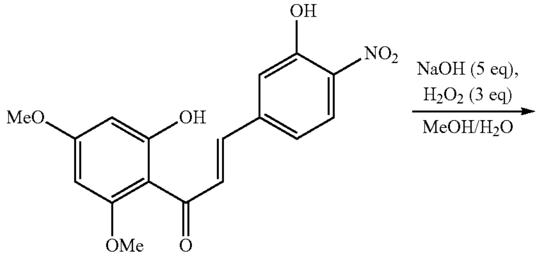
3
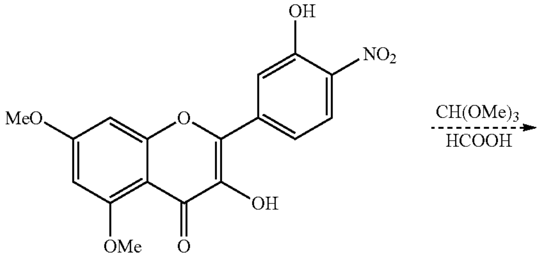
4
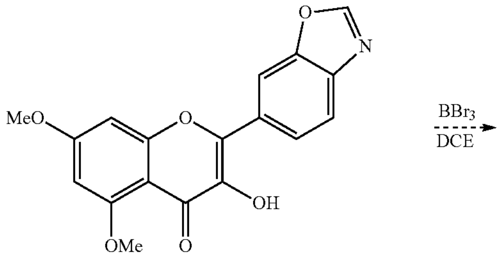
6
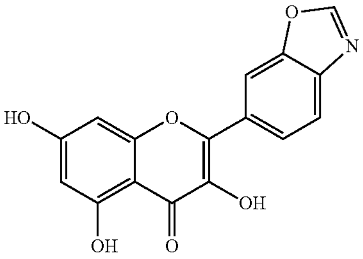
BBC0116
[Reaction Scheme 4]
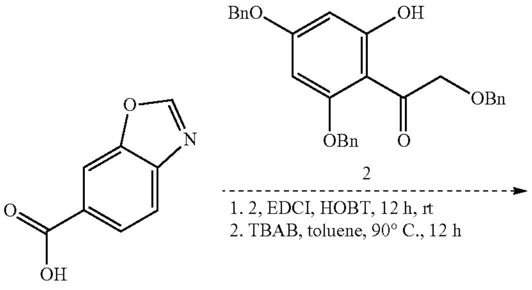
1
-continued
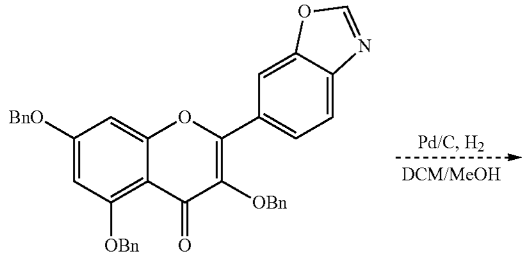
3
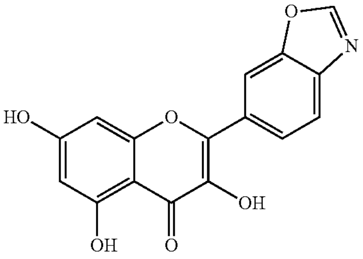
BBC0116
Compound 7 (BBC0116) was prepared by one of Reaction Schemes 1 to 4 above.
Example 8: Synthesis of Compound 8 (BBC0309)
[Reaction Scheme]
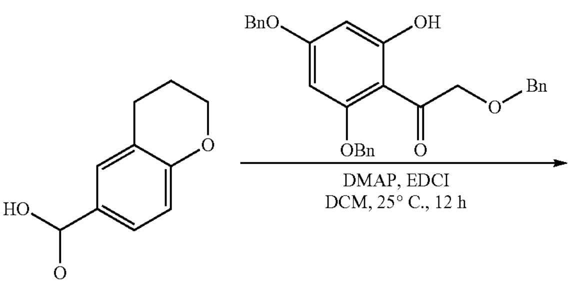
1
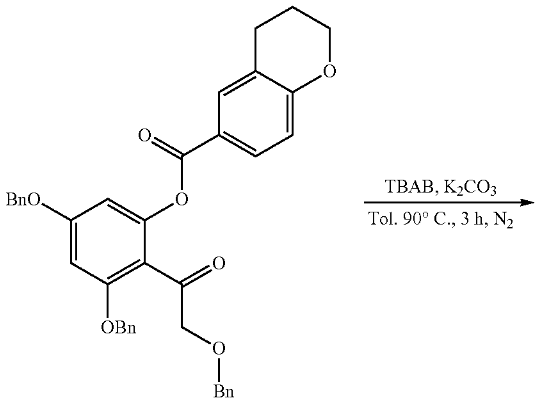
2

-continued

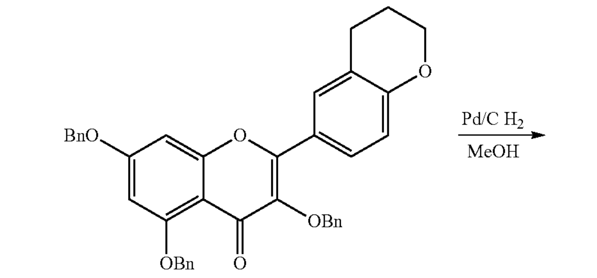

3

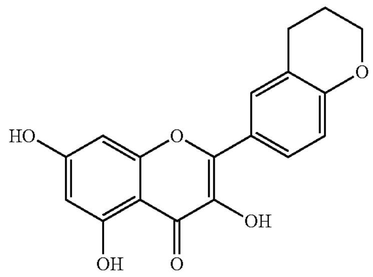

BBC0309

2-chromen-6-yl-3,5,7-trihydroxy-chromen-4-one (10.85 mg, 32.55 umol, 13.87% yield, 97.893% purity) was obtained from chromene-6-carboxylic acid 1 (55 mg, 308.67 umol, 2 eq).

LCMS: RT=2.857 min, m/z: 327.0 (M+H)+

$^1$H NMR (400 MHz, DMSO): δ (ppm) 12.44 (1H, s), 7.95-7.84 (2H, m), 6.88 (1H, d, J=8.40 Hz), 6.43 (1H, d, J=2.00 Hz), 6.18 (1H, d, J=2.00 Hz), 4.32-4.12 (2H, m), 2.82 (2H, t, J=6.00 Hz), 2.04-1.83 (2H, m)

Example 9: Synthesis of Compound 9 (BBC0310)

[Reaction Scheme]

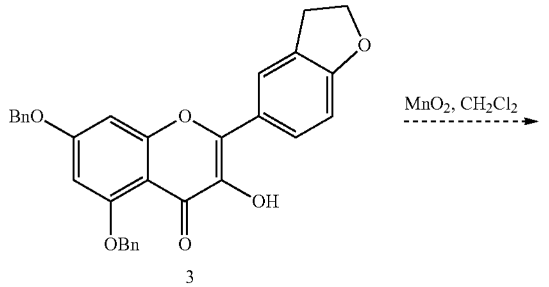

3

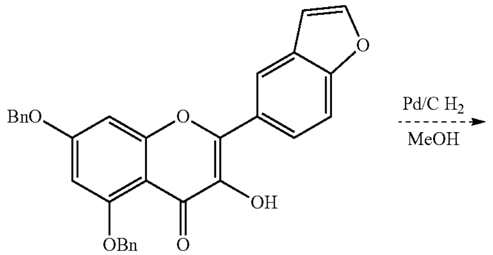

-continued

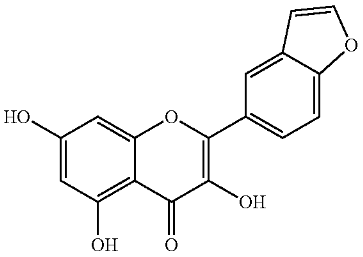

BBC0310

2-(benzofuran-5-yl)-3,5,7-trihydroxy-chromen-4-one (BBC0310) (19.45 mg, 61.51 umol, 14.88% yield, 98.112% purity) was obtained from benzofuran-5-carboxylic acid (143 mg, 881.94 umol, 2 eq) and 2-benzyloxy-1-(2,4-dibenzyloxy-6-hydroxyphenyl)ethanone (200 mg, 440.0. umol, 1 eq).

LCMS: RT=2.834 min, m/z: 311.0 (M+H)+

$^1$H NMR (400 MHz, DMSO): δ (ppm) 8.52 (1H, s), 8.16 (1H, d, J=8.8 Hz), 8.10 (1H, d, J=2.40 Hz), 7.77 (1H, d, J=8.80 Hz), 7.12 (1H, d, J=1.2 Hz), 6.48 (1H, d, J=2.0 Hz), 6.20 (1H, d, J=2.00 Hz).

Example 10: Synthesis of Compound 10 (BBC0311)

[Reaction Scheme]

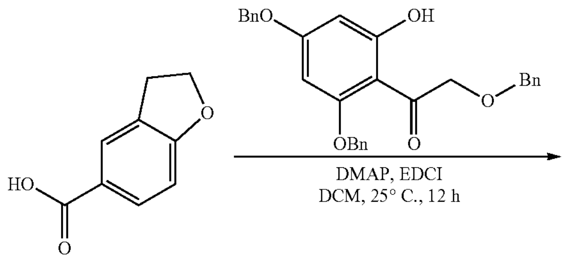

1

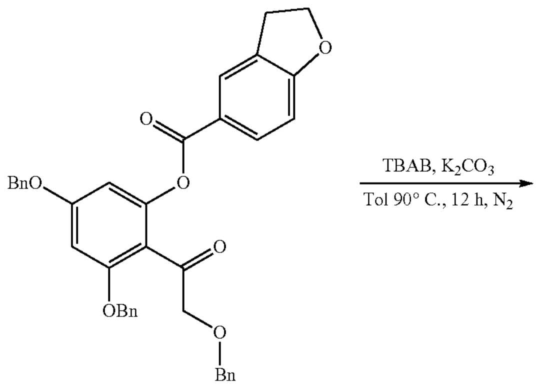

2

-continued

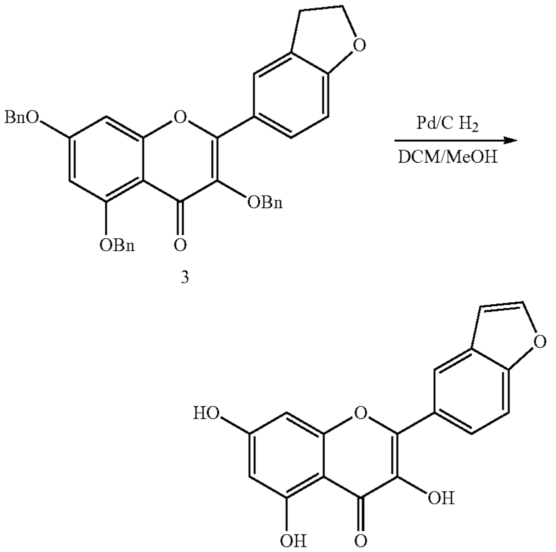

3

BBC0311

2-(2,3-dihydrobenzofuran-5-yl)-3,5,7-trihydroxy-chromen-4-one (BBC0311) (41.24 mg, 126.61 umol, 36.88% yield, 95.867% purity) was obtained from 2-benzyloxy-1-(2,4-dibenzyloxy-6-hydroxy-phenyl)ethanone (200 mg, 440.03 umol, 1 eq) and 2,3-dihydrobenzofuran-5-carboxylic acid (148.00 mg, 901.57 umol, 2.05 eq).

LCMS: RT=2.436 min, m/z: 313.0 (M+H)+

$^1$H NMR (400 MHz, MeOD): δ (ppm) 8.09 (1H, s), 8.01 (1H, dd, J=8.8, 1.6 Hz), 6.85 (1H, d, J=8.8 Hz), 6.40 (1H, d, J=2.0 Hz), 6.18 (1H, d, J=2.4 Hz), 4.63 (2H, t, J=8.8 Hz), 3.27 (2H, s).

Example 11: Synthesis of Compound 11 (BBC0312)

[Reaction Scheme]

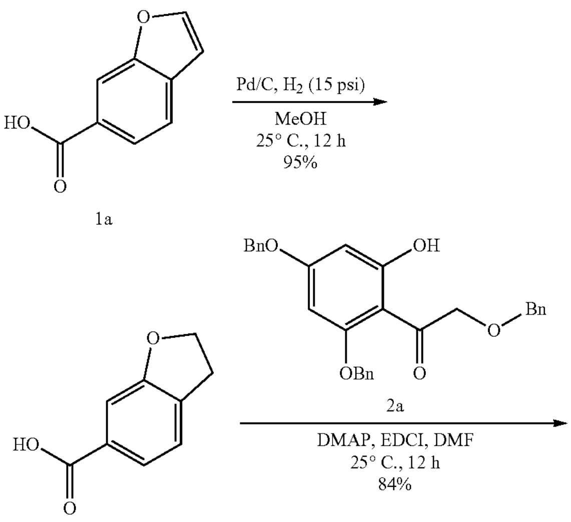

1a

2a

1

-continued

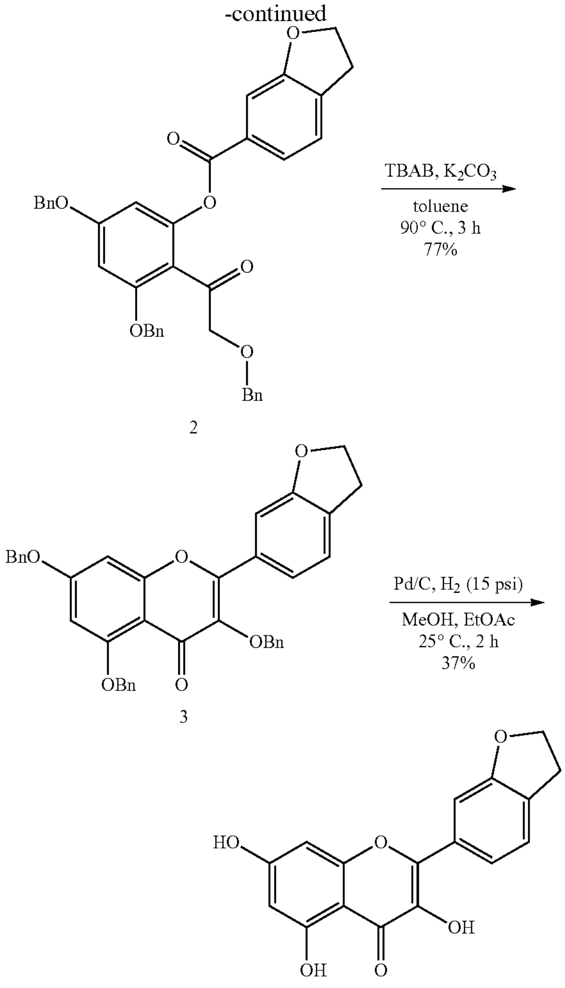

2

3

BBC0312

2-(2,3-dihydrobenzofuran-6-yl)-3,5,7-trihydroxy-chromen-4-one (BBC0312) (29.12 mg, 88.7 umol, 36.9% yield, 95.1% purity) was obtained from benzofuran-6-carboxylic acid (300.0 mg, 1.85 mmol, 1.0 eq).

LCMS: RT=2.762 min, m/z: 313.1 (M+H)+

$^1$H NMR (400 MHz, DMSO-$d_6$) δ ppm 12.36 (1H, s) 10.85 (1H, br s) 9.61 (1H, br s) 7.67 (1H, dd, J=8.0, 1.2 Hz) 7.53 (1H, d, J=1.2 Hz) 7.39 (1H, d, J=8.0 Hz) 6.46 (1H, d, J=2.0 Hz) 6.20 (1H, d, J=2.0 Hz) 4.58 (2H, t, J=8.8 Hz) 3.24 (2H, t, J=8.8 Hz).

Example 12: Synthesis of Compound 12 (BBC0313)

[Reaction Scheme]

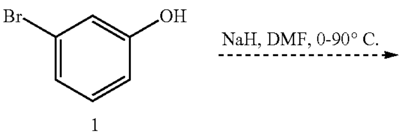

1
CAS 591-20-8
50 g/70 TMB

-continued

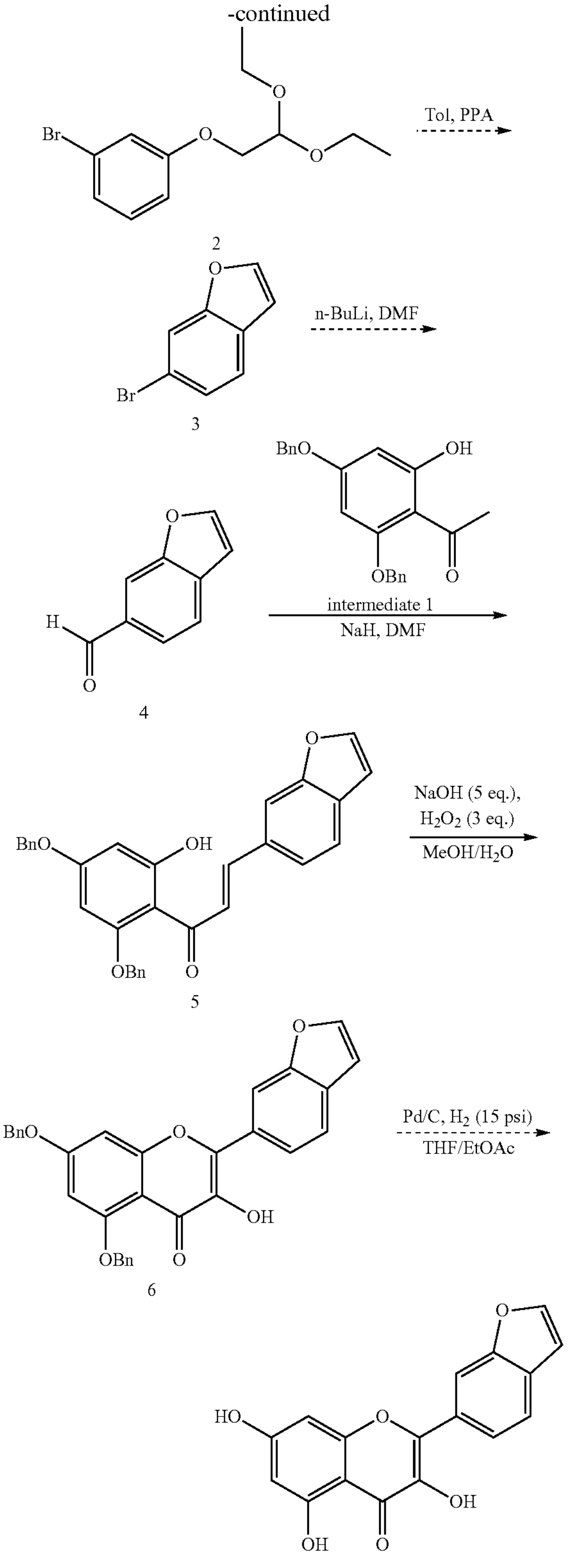

2

3

4

5

6

BBC0313

2-(benzofuran-6-yl)-3,5,7-trihydroxy-chromen-4-one (BBC0313) (13 mg, 40.7 umol, 26.3% yield, 97.1% purity) was obtained from 2-(3,4-dihydroxyphenyl)-3,5,7-trihydroxy-chromen-4-one (15.0 g, 49.6 mmol, 1.0 eq).

LCMS: RT=2.836 min, m/z: 97.1 (M+H)+

$^1$H NMR (400 MHz, DMSO-$d_6$) δ ppm 12.39 (1H, s) 8.43 (1H, s) 8.16 (1H, d, J=2.0 Hz) 8.11 (1H, dd, J=8.4, 1.6 Hz) 7.82 (1H, d, J=8.4 Hz) 7.07 (1H, dd, J=2.0, 0.8 Hz) 6.52 (1H, d, J=2.0 Hz) 6.22 (1H, d, J=2.0 Hz).

Example 13: Synthesis of Compound 13 (BBC0406)

[Reaction Scheme]

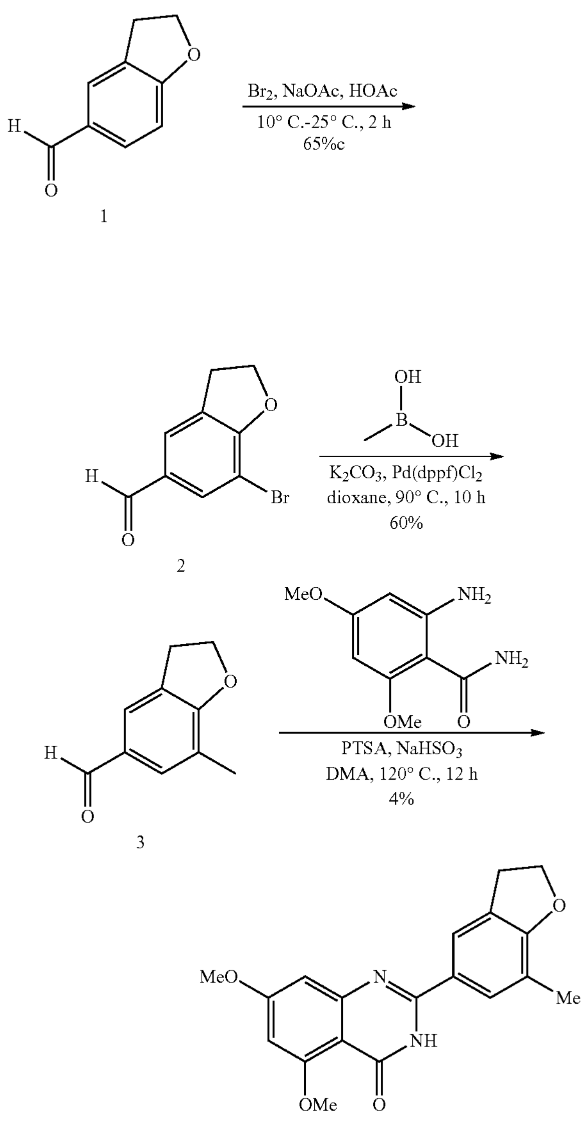

1

2

3

BBC0406

5,7-dimethoxy-2-(7-methyl-2,3-dihydrobenzofuran-5-yl)-3H-quinazolin-4-one (BBC0406) (13 mg, 38.11 umol, 4.15% yield, 99.2% purity) was obtained from 2,3-dihydrobenzofuran-5-carbaldehyde 1 (500 mg, 3.37 mmol, 1 eq).

LCMS: RT=2.200 min, m/z: 339.1 (M+H)+

$^1$H NMR (400 MHz, CHLOROFORM-d) δ ppm 8.98 (1H, br s), 7.71 (1H, s), 7.60 (1H, s), 6.80 (1H, d, J=2.4 Hz) 6.44 (1H, d, J=2.4 Hz), 4.68 (2H, t, J=8.8 Hz), 3.98 (3H, s), 3.92 (3H, s), 3.30 (2H, t, J=8.8 Hz), 2.28 (3H, s).

Example 14: Synthesis of Compound 14 (BBC0407)
[Reaction Scheme]
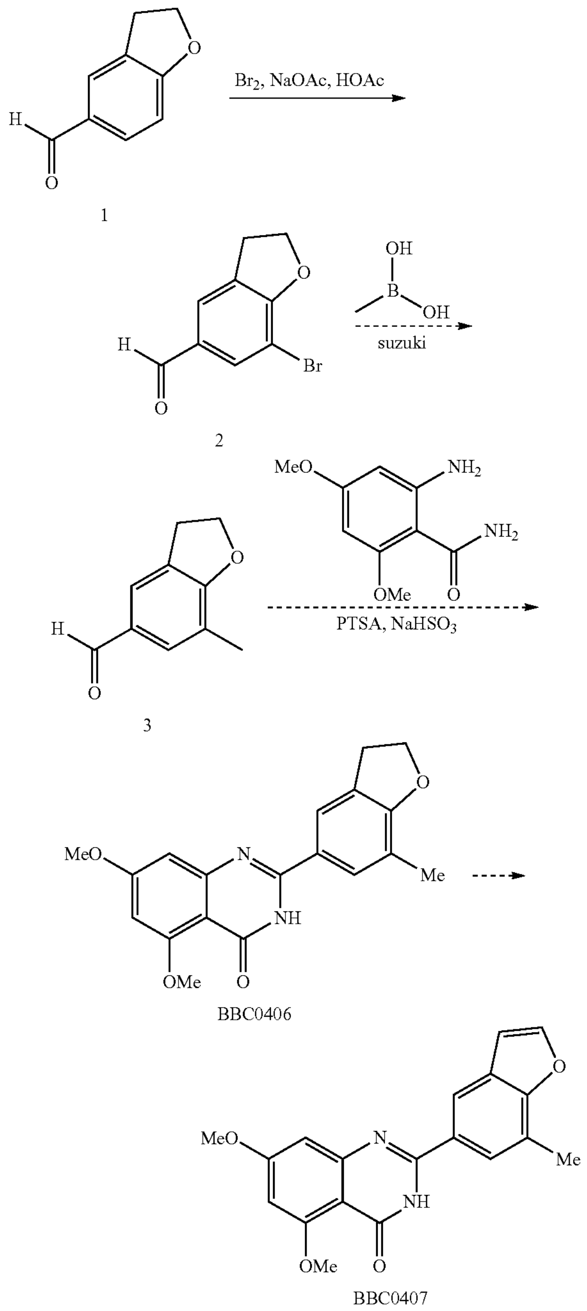
1
2
3
BBC0406
BBC0407
5,7-dimethoxy-2-(7-methylbenzofuran-5-yl)-3H-quinazolin-4-one (BBC0407) (6.77 mg, 19.14 umol, 43.17% yield, 95.070% purity) was obtained from 2,3-dihydrobenzofuran-5-carbaldehyde (1 g, 6.75 mmol, 1 eq).
LCMS: RT=2.264 min, m/z: 337.1 (M+H)+
$^1$H NMR (400 MHz, MeOD): δ (ppm) 8.15 (1H, s), 7.91 (1H, d, J=2.0 Hz), 7.85 (1H, s), 7.00 (1H, d, J=2.0 Hz), 6.86 (1H, d, J=2.0 Hz), 6.61 (1H, d, J=2.0 Hz), 3.96 (6H, m), 2.64 (3H, s).
Example 15: Synthesis of Compound 15 (BBC0301)
[Reaction Scheme]
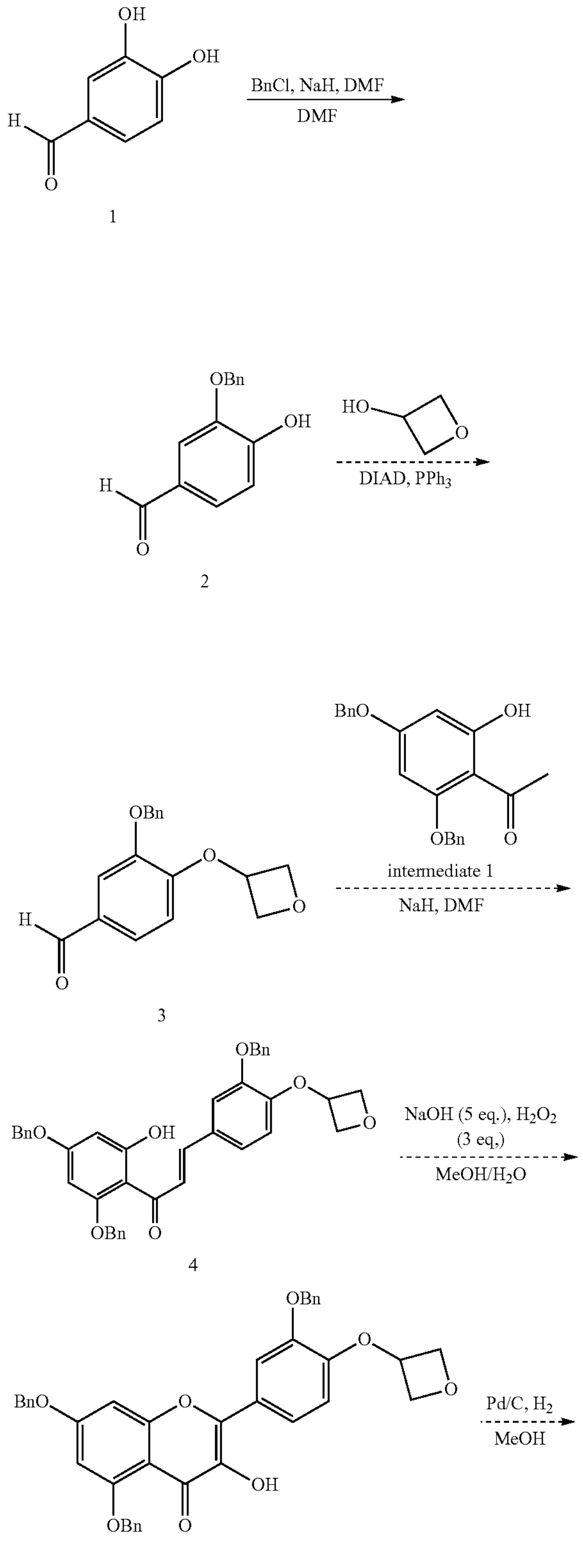
1
2
3
4
5

-continued

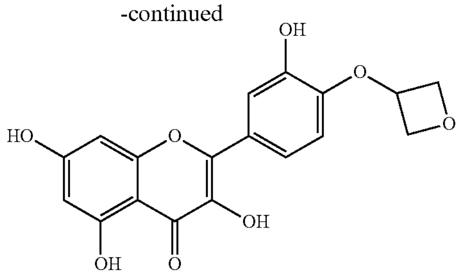

BBC0301

3,5,7-trihydroxy-2-[13-hydroxy-4-(oxetan-3-yloxy)phenyl]chromen-4-one (BBC0301) (5.57 mg, 15.3 umol, 19% yield, 98.3% purity) was obtained from 3,4-dihydroxybenzaldehyde (1.0 g, 7.24 mmol, 1.0 eq).

LCMS: RT=2.465 min m/z: 359.0 (M+H)+

$^1$H NMR (400 MHz, DMSO-d6) δ ppm 12.43 (1H, s) 10.82 (1H, s) 9.47-9.54 (2H, m) 7.72 (1H, d, J=2.4 Hz) 7.58 (1H, dd, J=8.8, 2.4 Hz) 6.74 (1H, d, J=8.8 Hz) 6.42 (1H, d, J=2.0 Hz) 6.20 (1H, d, J=2.0 Hz) 5.32 (1H, t, J=5.6 Hz) 4.94 (2H, t, J=6.8 Hz) 4.61 (2H, dd, J=7.6, 5.2 Hz).

Example 16: Synthesis of Compound 16 (BBC0302)

[Reaction Scheme]

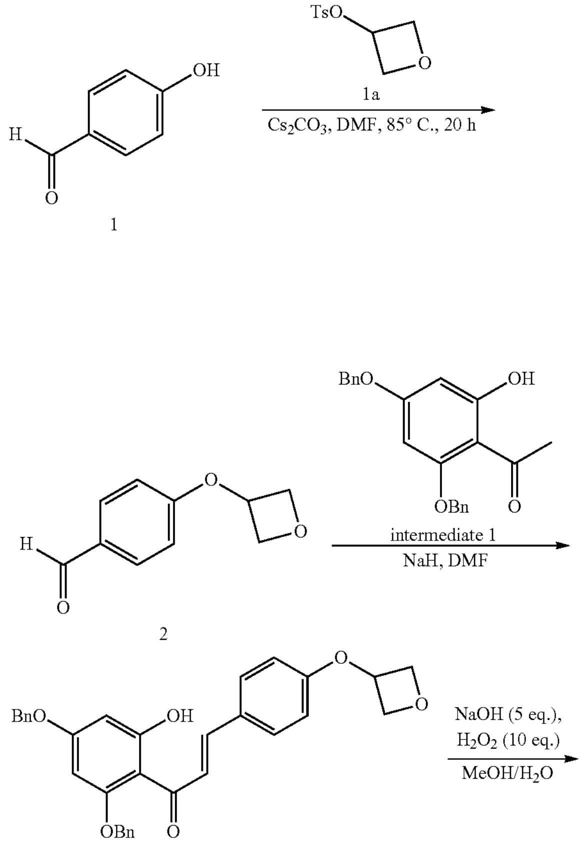

1, 2, 3

-continued

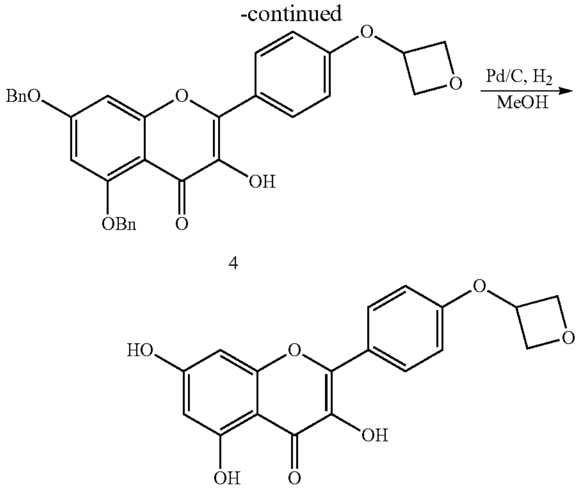

4

BBC0302

3,5,7-trihydroxy-2-[4-(oxetan-3-yloxy)phenyl]chromen-4-one (1.69 mg, 4.49 umol, 46.95% yield, 91% purity) was obtained from 4-hydroxybenzaldehyde 1 (65 mg, 532.26 umol, 1.21 eq).

LCMS: RT=2.792 min, m/z: 343.1 (M+H)+

$^1$H NMR (400 MHz, CD3OD) δ 8.19 (2H, d, J=8.8 Hz), 6.91 (2H, d, J=8.8 Hz), 6.41 (1H, d, J=2.0 Hz), 6.19 (1H, d, J=2.0 Hz), 5.41-5.35 (1H, m), 5.08-5.04 (2H, m), 6.74-4.69 (2H, m).

Example 17: Synthesis of Compound 17 (BBC0303)

[Reaction Scheme]

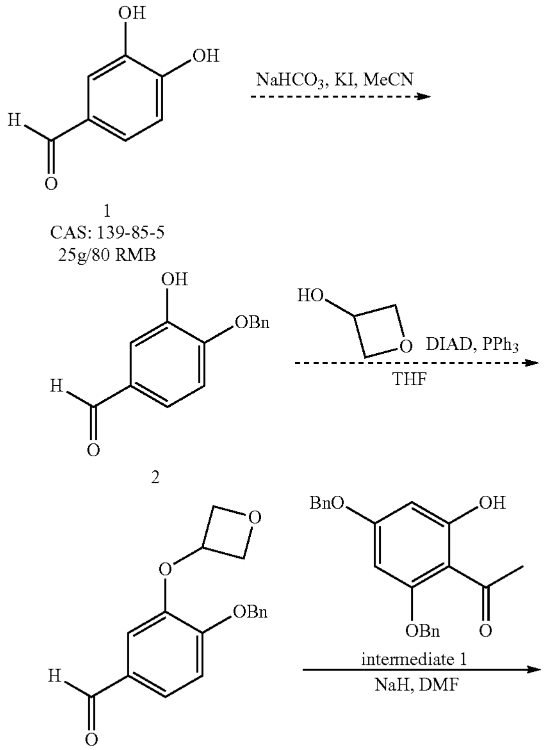

2, 3

-continued
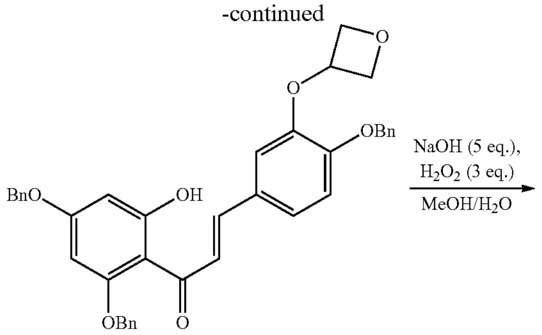
4
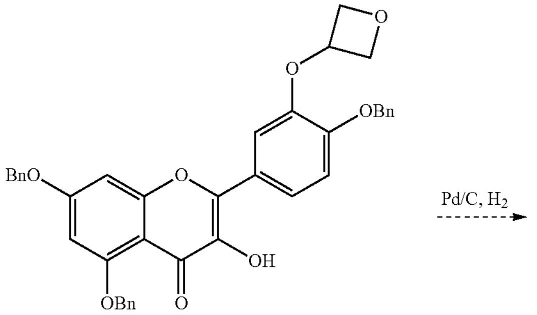
5
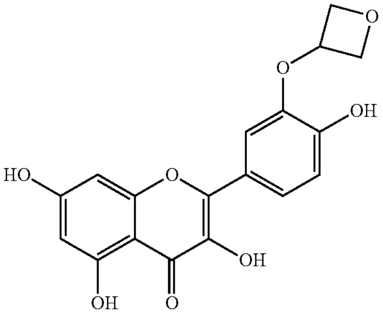
BBC0303
3,5,7-trihydroxy-2-[4-hydroxy-3-(oxetan-3-yloxy)phenyl]chromen-4-one (BBC0303) (5.11 mg, 13.41 umol, 9.6% yield, 94% purity) was obtained from 3,4-dihydroxybenzaldehyde (200.0 mg, 1.45 mmol, 1.0 eq).
LCMS: RT=2.471 min, m/z: 359.0 (M+H)+
$^1$H NMR (400 MHz, DMSO-d6) δ ppm 10.79 (1H, s) 9.93 (1H, s) 9.46 (1H, s) 7.70 (1H, dd, J=8.4, 2.0 Hz) 7.45 (1H, d, J=2.0 Hz) 6.99 (1H, d, J=8.4 Hz) 6.48 (1H, d, J=2.0 Hz) 6.19 (1H, d, J=2.0 Hz) 5.29 (1H, t, J=5.6 Hz) 4.91 (2H, t, J=6.8 Hz) 4.66 (2H, dd, J=7.6, 5.6 Hz).
Example 18: Synthesis of Compound 18 (BBC0305)
Reaction Scheme]
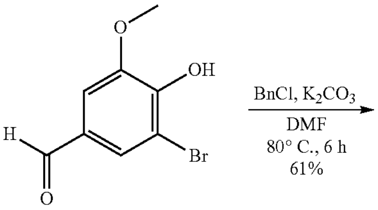
1
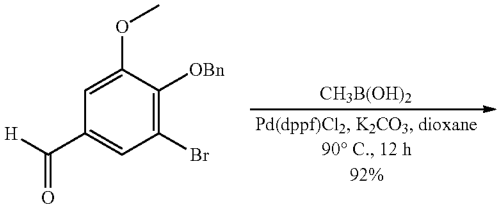
2
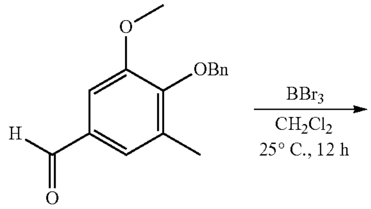
3
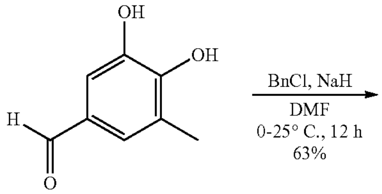
4
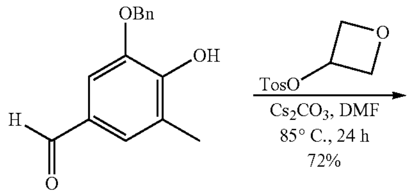
5
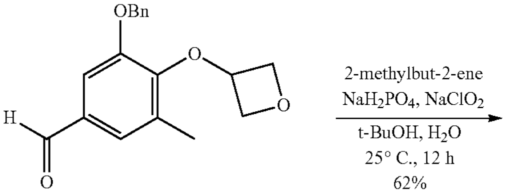
6

-continued
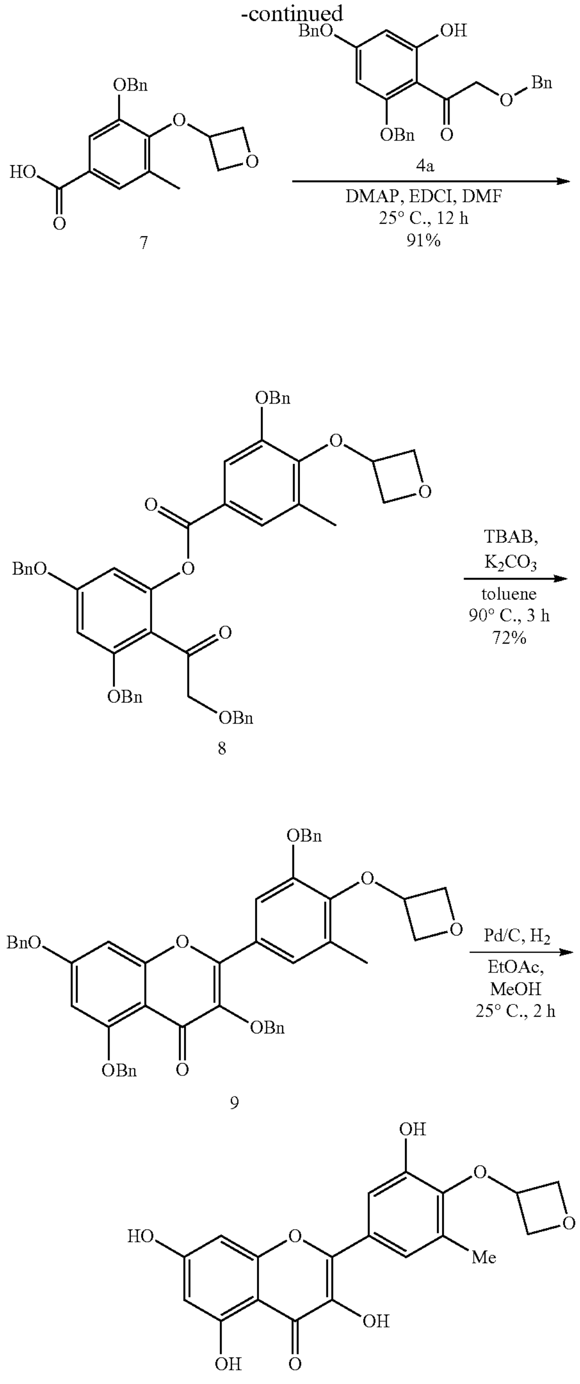
7, 4a, 8, 9
BBC0305
3,5,7-trihydroxy-2-[3-hydroxy-5-methyl-4-(oxetan-3-yloxy)phenyl]chromen-4-one (BBC0305) (6 mg, 15.79 umol, 98% purity) was obtained from 3-bromo-4-hydroxy-5-methoxy-benzaldehyde 1 (2.0 g, 8.66 mmol, 1.7 mL, 1.0 eq).
LCMS: RT=2.607 min, m/z: 373.1 (M+H)+
$^1$H NMR (400 MHz, DMSO-d6) δ ppm 12.31-12.49 (1H, m) 9.65-9.90 (1H, m) 7.59 (1H, d, J=2.0 Hz) 7.45 (1H, d, J=1.6 Hz) 6.39 (1H, d, J=2.0 Hz) 6.18 (1H, d, J=2.0 Hz) 5.14 (1H, t, J=5.6 Hz) 4.73-4.81 (2H, m) 4.64-4.71 (2H, m) 2.24 (3H, s).
Example 19: Synthesis of Compound 19 (BBC0306)
[Reaction Scheme]
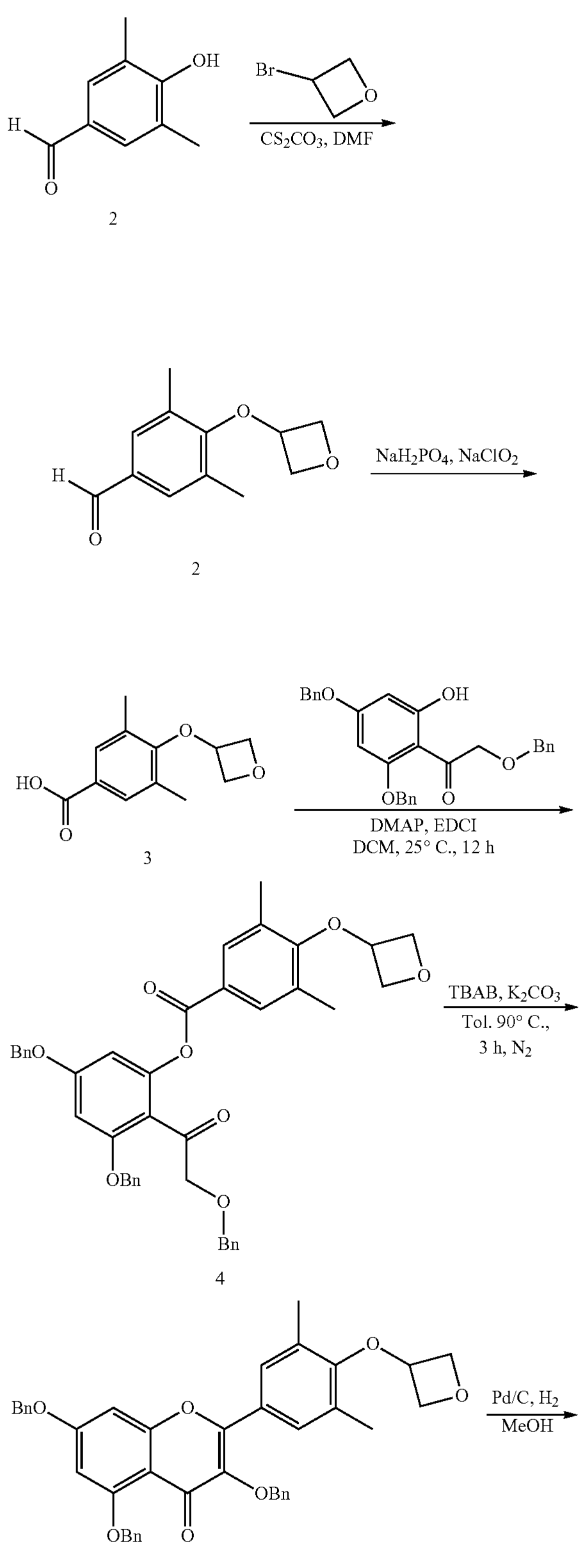
2, 2, 3, 4, 5

-continued

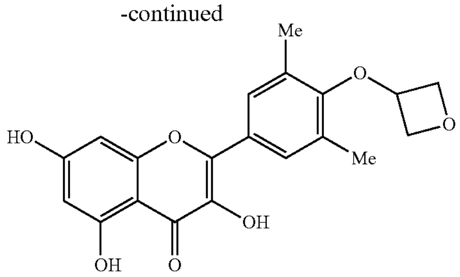

BBC0306

2-[3,5-dimethyl-4-(oxetan-3-yloxy)phenyl]-3,5,7-trihydroxy-chromen-4-one (BBC0306) (23.28 mg, 61.68 umol, 15.81% yield, 98.128% purity) was obtained from 4-hydroxy-3,5-dimethyl-benzaldehyde 1 (1 g, 6.66 mmol, 1 eq).

LCMS: RT=2.876 min, m/z: 371.0 (M+H)+

$^1$H NMR (400 MHz, DMSO): δ (ppm) 7.85 (2H, s), 6.44 (1H, d, J=2.00 Hz), 6.18 (1H, d, J=2.00 Hz), 4.94 (1H, q, J=6.20 Hz), 4.83 (2H, t, J=6.40 Hz), 4.80-4.76 (2H, m), 2.23 (6H, s).

Example 20: Synthesis of Compound 20 (BBC0307)

Reaction Scheme]

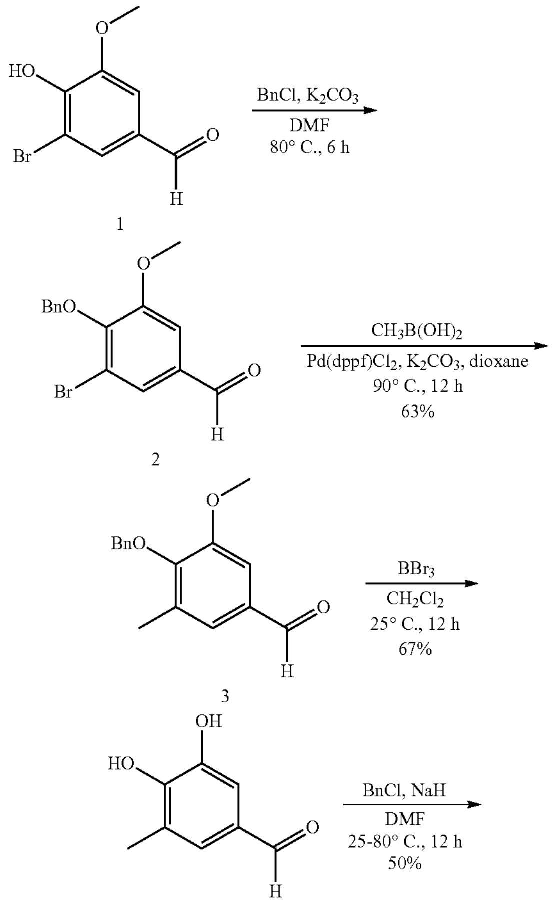

1

2

3

4

-continued

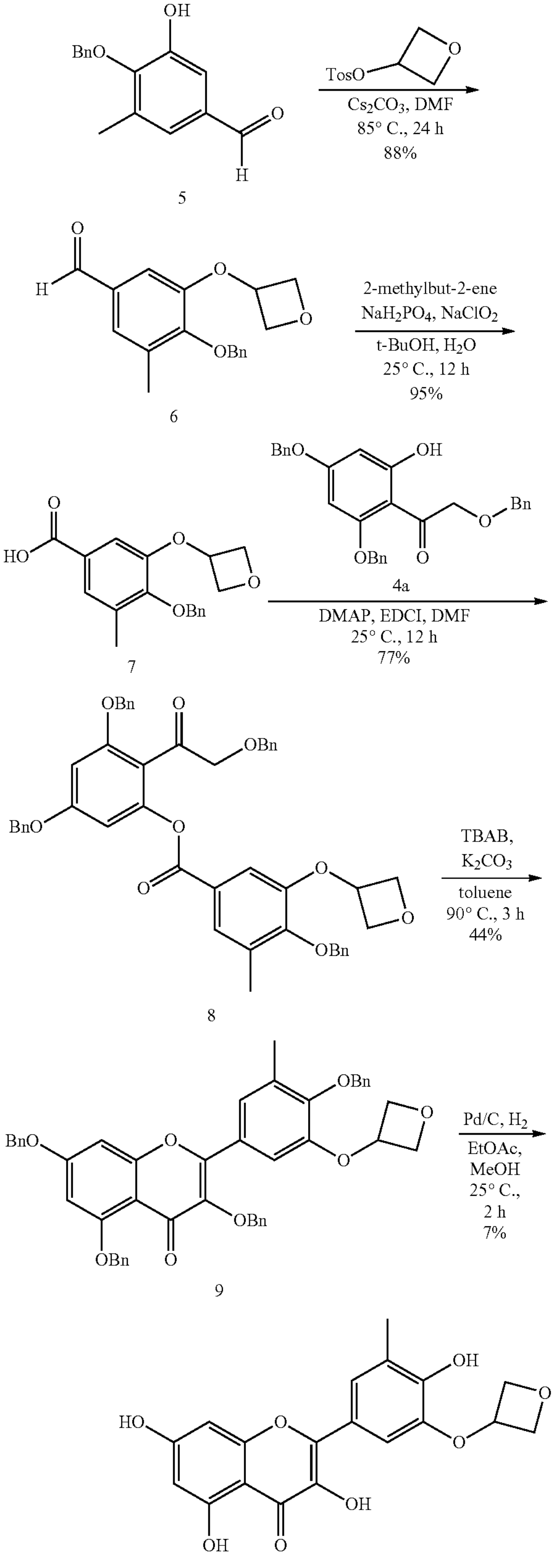

5

6

7

8

9

BBC0307

3,5,7-trimethoxy-2-[4-hydroxy-3-methyl-5-(oxetan-3-yloxy)phenyl]chromen-4-one (BBC0307) (5.99 mg, 15.0 umol, 6.9% yield, 93.5% purity) was obtained from 3-bromo-4-hydroxy-5-methoxy-benzaldehyde 1 (2.0 g, 8.66 mmol, 1.7 mL, 1.0 eq).

LCMS: RT=2.654 min, m/z: 373.1 (M+H)+

$^1$H NMR (400 MHz, DMSO-d6) δ ppm 12.44 (1H, br d, J=1.6 Hz) 7.62 (1H, s) 7.31 (1H, s) 6.47 (1H, d, J=2.0 Hz) 6.17 (1H, d, J=2.0 Hz) 5.30 (1H, br t, J=5.6 Hz) 4.91 (2H, t, J=6.8 Hz) 4.65-4.72 (2H, m) 2.22 (3H, s).

Example 21: Synthesis of Compound 21 (BBC0104)

[Reaction Scheme]

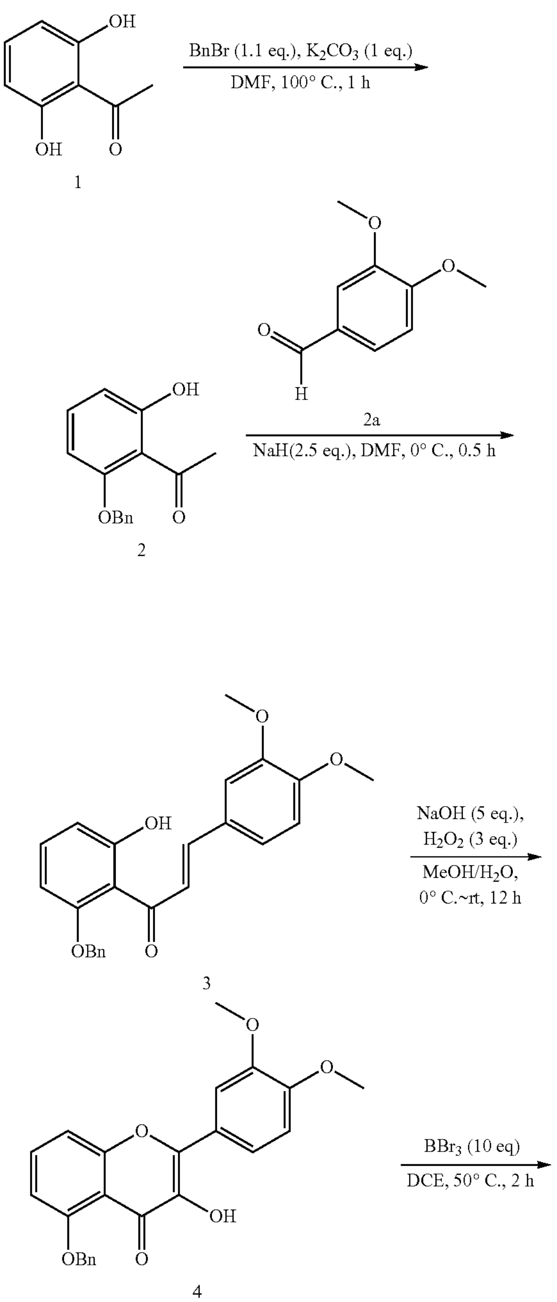

1

2

3

4

-continued

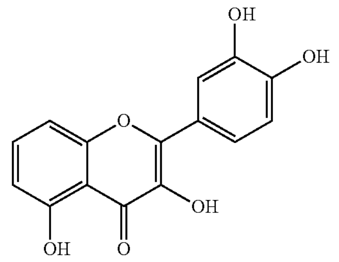

BBC0104

2-(3,4-dihydroxyphenyl)-3,5-dihydroxy-chromen-4-one (BBC0104) (19 mg, 64.89 umol, 52.48% yield, 97.75% purity) was obtained from 1-(2,6-dihydroxyphenyl)ethanone 1 (1.0 g, 6.57 mmol, 1.0 eq).

LCMS: RT=0.735 min, m/z: 287 (M+H)+

$^1$H NMR (400 MHz, DMSO-d6) δ ppm 12.41 (1H, s), 9.60 (2H, br s), 9.35 (1H, br s), 7.74 (1H, d, J=2.0 Hz), 7.58-7.65 (2H, m), 7.12 (1H, d, J=8.0 Hz), 6.91 (1H, d, J=8.0 Hz), 6.76 (1H, d, J=8.0 Hz).

Example 22: Synthesis of Compound 22 (BBC0105)

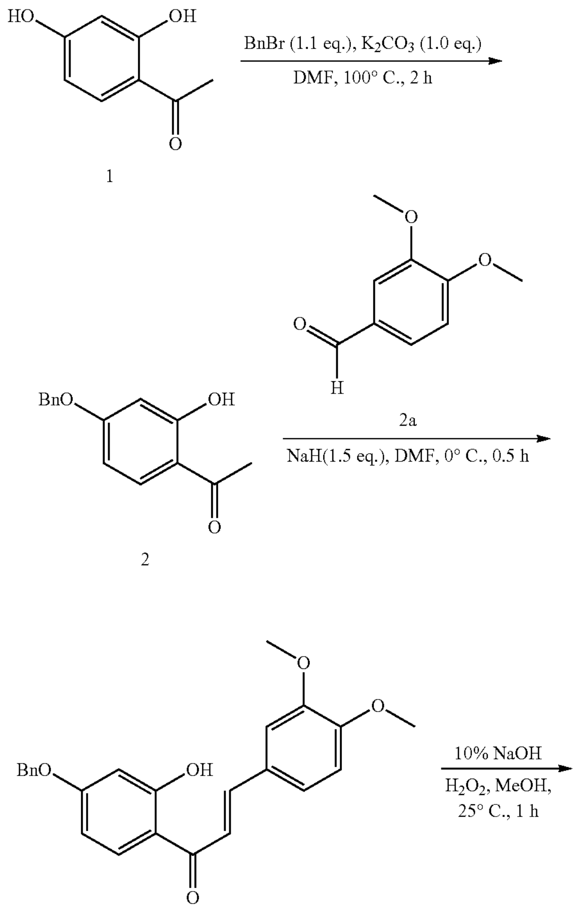

1

2

3

-continued

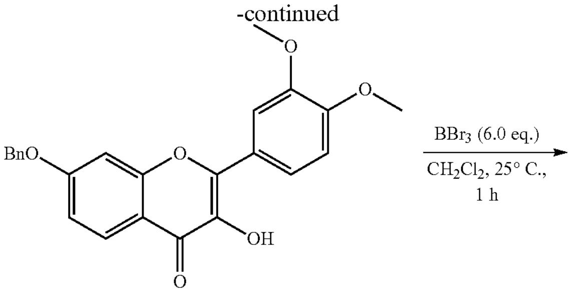

4

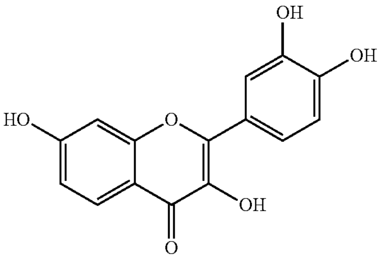 [SMILES: O=c1c(O)c(-c2ccc(O)c(O)c2)oc2cc(O)ccc12]

BBC0105

2-(3,4-dihydroxyphenyl)-3,7-dihydroxy-chromen-4-one (BBC0105) (12.0 mg, 39.95 umol, 40.4% yield, 95.3% purity) was obtained from 1-(2,4-dihydroxyphenyl)ethanone 1 (1.0 g, 6.57 mmol, 847.5 uL, 1.0 eq).

LCMS: RT=3.420 min, m/z: 287.0 (M+H)+

$^{1}H$ NMR (400 MHz, METHANOL-d4) δ ppm 7.99 (1H, d, J=9.2 Hz) 7.77 (1H, d, J=2.0 Hz) 7.67 (1H, dd, J=8.4, 2.00 Hz) 6.88-6.95 (3H, m).

Comparative Example

The compounds of Comparative Examples 1 to 3 were purchased from WUXI APPTEC (SHANGHAI) CO. LTD and compared with the novel quercetin compounds of the present invention in terms of BET inhibitory effect.

| Comparative Example | Structure |
|---|---|
| 1 | 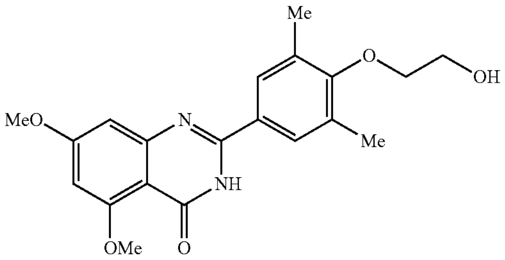 [SMILES: COc1cc(OC)c2c(=O)[nH]c(-c3cc(C)c(OCCO)c(C)c3)nc2c1] RVX-208 |
| 2 | 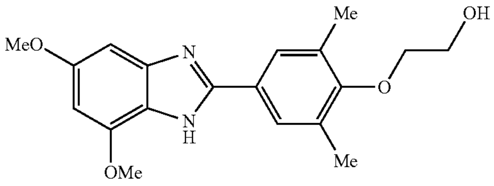 [SMILES: COc1cc(OC)c2[nH]c(-c3cc(C)c(OCCO)c(C)c3)nc2c1] BBC0206 |

-continued

| Comparative Example | Structure |
|---|---|
| 3 | 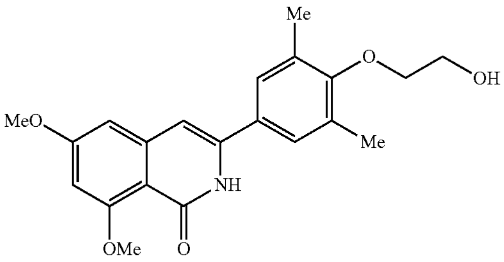 BBC0204 |

[Test Example]

In order to evaluate the ability to inhibit the interaction between the bromodomains of BRD2 (BD1, BD2, BD1+BD2), BRD3 (BD1, BD2, BD1+BD2), and BRD4 (BD1, BD2, BD1+BD2), which are one of the BET protein families, and tetraacetylated histone H4 peptides by the novel compounds according to the present invention, the following experiments were performed.

Test Example 1: Binding Inhibitory Effect on BRD2 Protein

The binding inhibitory effect of the compounds of the present invention and the compounds of comparative examples on the BRD2 protein among the BET proteins was tested as follows.

The compounds were diluted 1:5 serial dilutions in an assay buffer from a 10 mM stock in DMSO (starting concentration of 100 μM) in a white OptiPlate-384 (PerkinElmer). A mixture composed of 100 nM GST-BRD2 (BD1, BD2, BD1+BD2) and 100 nM biotinylated acetyl-histone H4 (Lys5, 8, 12, 16) peptide was prepared in an assay buffer (50 mM HEPES pH 7.4; 25 mM NaCl; 0,05% Tween 20; 0.1% bovine serum albumin (BSA); 10 mM dithiothreitol (DTT)). 6 μl of the mixture was added to the dilution, and then 6 μl of the pre-mixed AlphaLISA Glutathione Acceptor Beads and AlphaScreen Streptavidin Donor Beads from PerkinElmer in an assay buffer at a concentration of 10 μg/ml, respectively, was added, and the samples were incubated with shaking at 300 rpm for 30 minutes at room temperature in the dark. Thereafter, the signals were measured with a PerkinElmer Envision HTS Multilabel Reader using an AlphaScreen protocol of PerkinElmer. Each plate contained a negative control group in which biotinylated acetyl-histone H4 peptide and GST-BRD2 (BD1, BD2, BD1+BD2) were drained and replaced with an assay buffer.

Figure 2:
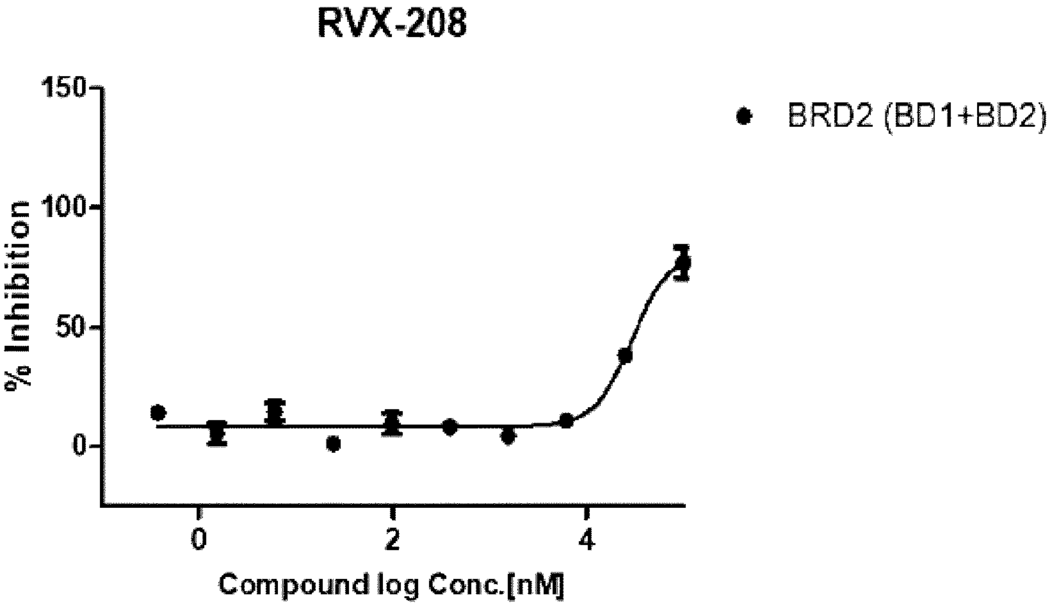
FIG. 2 is a graph showing the inhibitory activity of BRD2 (BD1+BD2) protein binding by the compound of Comparative Example 1 (RVX-208).

When the software GraphPad Prism was used for calculation, a value of a negative control group was input as a low reference value. In addition, a positive control group (a probe molecule I-BET762 having a protein/peptide mixture) was pipetted. Determination of IC50 values was performed using GraphPad Prism 3.03 software (or an updated version thereof), and the results are shown in Table 1 below, and FIGS. 1 and 2.

TABLE 1

| | Compound | BRD2 (BD1) | BRD2 (BD2) | BRD2 (BD1 + BD2) |
|---|---|---|---|---|
| Comparative Example 1 | RVX-208 | 32,005 | 1,643 | 29,360 |
| Comparative Example 2 | BBC0206 | 65,151 | >50,000 | >20,000 |
| Comparative Example 3 | BBC0204 | 29,758 | 5,344 | 73,431 |
| Example 1 | BBC0109 | 8,626 | — | 9,702 |
| Example 2 | BBC0110 | 9,060 | — | — |
| Example 4 | BBC0113 | 12,248 | 5115 | — |
| Example 5 | BBC0114 | 4,136 | — | — |
| Example 6 | BBC0115 | 5,238 | — | — |
| Example 8 | BBC0309 | 7,035 | — | — |
| Example 9 | BBC0310 | 10,080 | — | — |
| Example 10 | BBC0311 | 5,850 | 3,792 | — |
| Example 11 | BBC0312 | 3,686 | — | — |
| Example 12 | BBC0313 | 4,627 | 499 | — |
| Example 15 | BBC0301 | 16,946 | — | — |
| Example 16 | BBC0302 | 2,399 | — | — |
| Example 17 | BBC0303 | 8,348 | — | — |
| Example 18 | BBC0305 | 6,547 | — | — |
| Example 19 | BBC0306 | 2,706 | — | — |
| Example 20 | BBC0307 | 18,481 | — | — |
| Example 21 | BBC0104 | 8,518 | — | — |
| Example 22 | BBC0105 | 8,885 | — | — |

As shown in Table 1 above, it was confirmed that all of the compounds of examples of the present invention had excellent inhibitory activity against the BRD2 protein, as compared to the compound of Comparative Example 1. In particular, it can be seen that the compound of Example 1 has an IC50 value of BRD2 (BD1) and BRD2 (BD1+BD2) of about 30% as compared to the compound of Comparative Example 1. In particular, it can be seen that the compounds of Examples 11 and 19 have an IC50 value of BRD2 (BD1) of less than 10% as compared to the compound of Comparative Example 1. Therefore, the compounds of the present invention have a more excellent inhibitory effect on the BRD2 protein than the conventional BET inhibitor (RVX-208).

Test Example 2: Binding Inhibitory Effect on BRD3 Protein

In the same manner as in Test Example 1 above, an experiment was performed to confirm the binding inhibitory effect of the compounds of the present invention and the compounds of comparative examples on the BRD3 (BD1, BD2, BD1+BD2) protein. The results are shown in Table 2 below.

TABLE 2

| | Compound | BRD3 (BD1) | BRD3 (BD2) | BRD3 (BD1 + BD2) |
|---|---|---|---|---|
| Comparative Example 1 | RVX-208 | 23,398 | 2,033 | >100,000 |
| Comparative Example 2 | BBC0206 | >50,000 | >150,000 | >50,000 |
| Comparative Example 3 | BBC0204 | 45,280 | — | >100,000 |
| Example 1 | BBC0109 | — | — | 20,776 |
| Example 2 | BBC0110 | — | — | 20,097 |
| Example 4 | BBC0113 | 17,075 | — | — |
| Example 5 | BBC0114 | 7,983 | — | 51,347 |
| Example 6 | BBC0115 | 7,180 | — | 86,037 |
| Example 8 | BBC0309 | 1,461 | — | — |
| Example 9 | BBC0310 | 3,261 | — | — |
| Example 10 | BBC0311 | 7,200 | — | — |
| Example 11 | BBC0312 | 2,640 | — | — |

TABLE 2-continued

| | Compound | BRD3 (BD1) | BRD3 (BD2) | BRD3 (BD1 + BD2) |
|---|---|---|---|---|
| Example 12 | BBC0313 | 1,897 | — | — |
| Example 13 | BBC0406 | 11,136 | — | — |
| Example 15 | BBC0301 | — | — | 29,362 |
| Example 17 | BBC0303 | 3,181 | — | 95,569 |
| Example 18 | BBC0305 | 3,002 | — | — |
| Example 19 | BBC0306 | 1,412 | 1,344 | — |
| Example 20 | BBC0307 | 9,291 | — | — |

As shown in Table 2 above, it was confirmed that all of the compounds of examples of the present invention had excellent inhibitory activity against the BRD3 protein, as compared to the compound of Comparative Example 1. In particular, it can be seen that the compound of Example 1 has a much lower IC50 value of BRD3 (BD1+BD2) as compared to the compound of Comparative Example 1. In particular, it can be seen that the compounds of Examples 12 and 19 have an IC50 value of BRD3 (BD1) of less than 10% as compared to the compound of Comparative Example 1. Therefore, the compounds of the present invention have a more excellent inhibitory effect on the BRD3 protein than the conventional BET inhibitor (RVX-208).

Test Example 3: Binding Inhibitory Effect on BRD4 Protein

Figure 3:
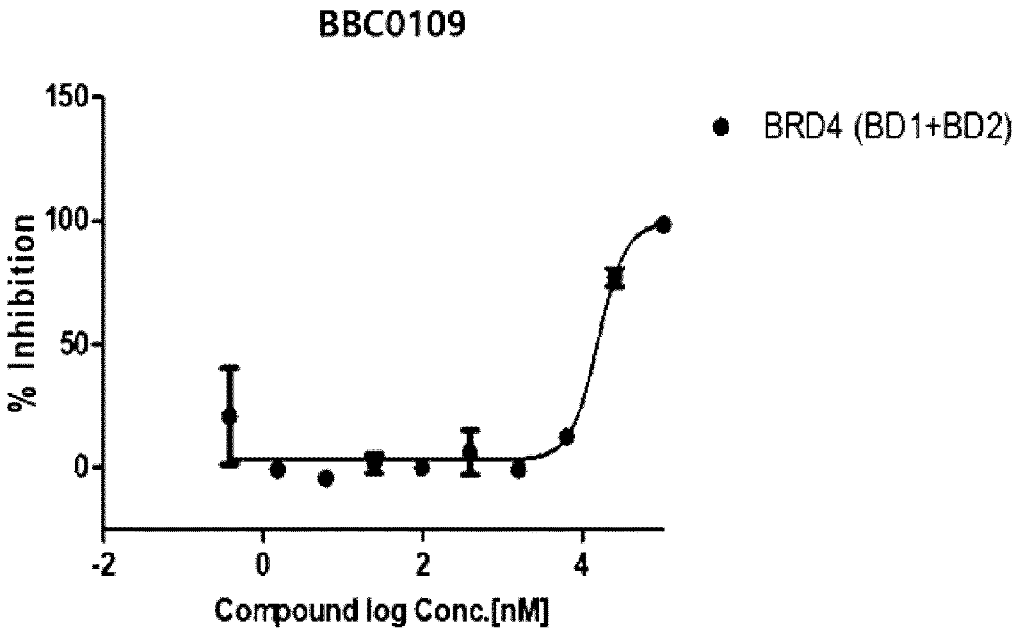
FIG. 3 is a graph showing the inhibitory activity of BRD4 (BD1+BD2) protein binding by Compound 1 of the present invention (BBC0109).
Figure 4:
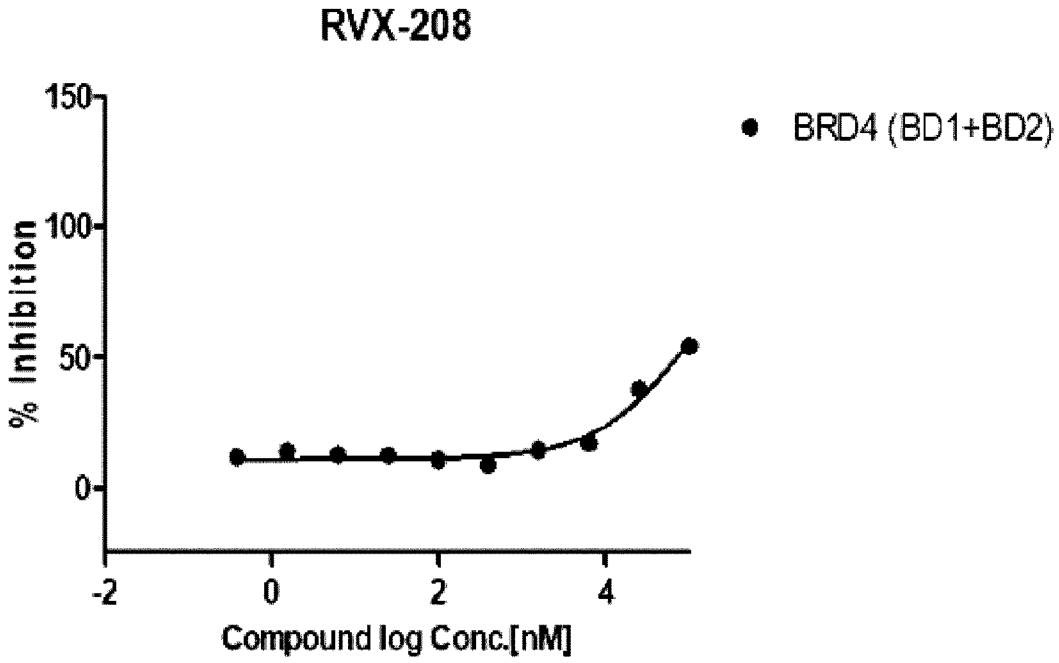
FIG. 4 is a graph showing the inhibitory activity of BRD4 (BD1+BD2) protein binding by the compound of Comparative Example 1 (RVX-208).

In the same manner as in Test Example 1 above, an experiment was performed to confirm the binding inhibitory effect of the compounds of the present invention and the compounds of comparative examples on the BRD4 (BD1, BD2, BD1+BD2) protein. The results are shown in Table 3 below, and FIGS. 3 and 4.

TABLE 3

| | Compound | BRD4 (BD1) | BRD4 (BD1 + BD2) |
|---|---|---|---|
| Comparative Example 1 | RVX-208 | 23,656 | 97,219 |
| Comparative Example 2 | BBC0206 | >50,000 | >20,000 |
| Comparative Example 3 | BBC0204 | 35,138 | 97,174 |
| Example 1 | BBC0109 | — | 15,579 |
| Example 2 | BBC0110 | 15,519 | 38,634 |
| Example 15 | BBC0301 | — | 30,270 |
| Example 20 | BBC0307 | — | 87,294 |

As shown in Table 3 above, it was confirmed that all of the compounds of examples of the present invention had excellent inhibitory activity against the BRD4 protein, as compared to the compound of Comparative Example 1. In particular, it can be seen that the compound of Example 1 has a much lower IC50 value of BRD4 (BD1+BD2) as compared to the compound of Comparative Example 1. Therefore, the compounds of the present invention have a more excellent inhibitory effect on the BRD4 protein than the conventional BET inhibitor (RVX-208).

As a result, all of the compounds of the present invention have excellent inhibitory activity against the proteins of BRD2 (BD1, BD2, BD1+BD2), BRD3 (BD1, BD2, BD1+BD2), and BRD4 (BD1, BD2, BD1+BD2), and thus can be effectively used for the treatment and prevention of BET-related diseases.

The invention claimed is:

1. A compound represented by formula 1 below or a pharmaceutically acceptable salt thereof:

[Formula 1]

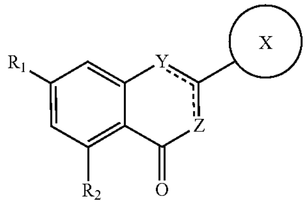

in the formula, ring X is

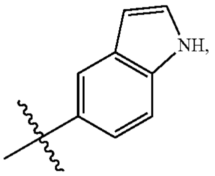

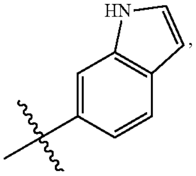

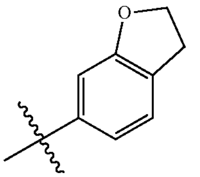

or

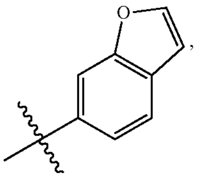

Y is O,

Z is $CR_5$,

---- is each absent or a single bond, $R_1$, $R_2$, and $R_5$ are each independently H or —ORa, Ra is each independently H or $C_1$-$C_6$ alkyl.

2. A compound selected from the group consisting of the following compounds or a pharmaceutically acceptable salt thereof:

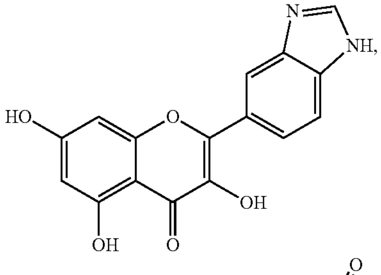

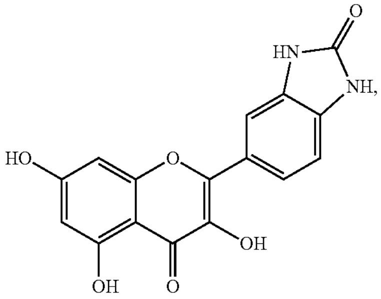

-continued

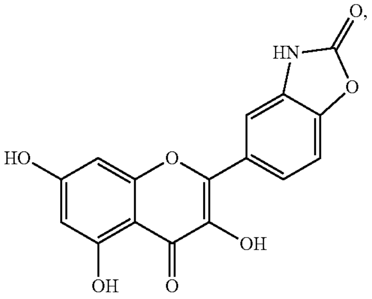

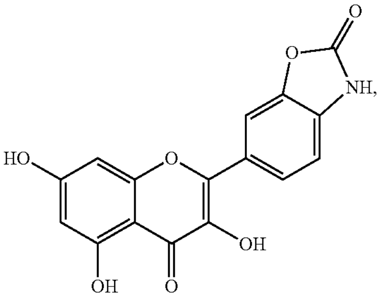

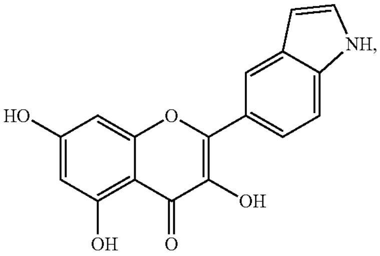

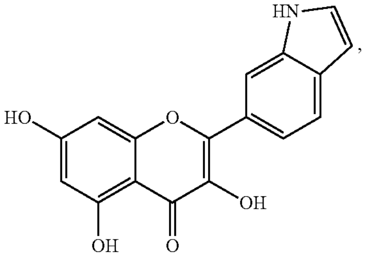

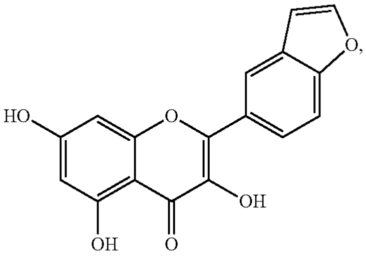

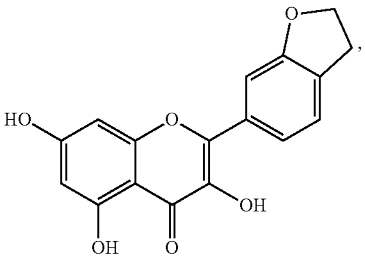

-continued
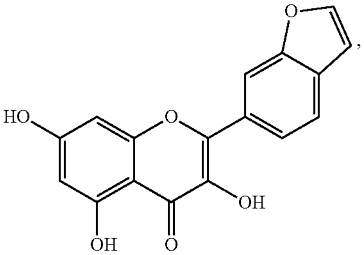
,
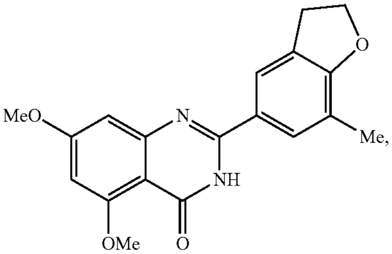
,
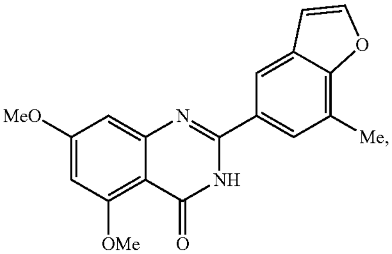
,
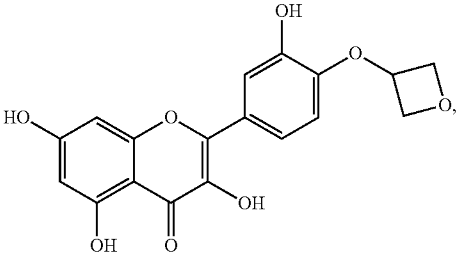
,
-continued
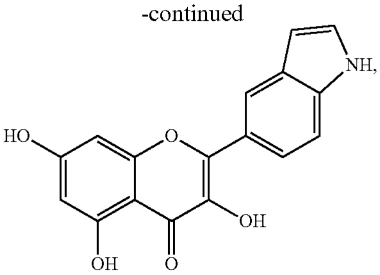
,
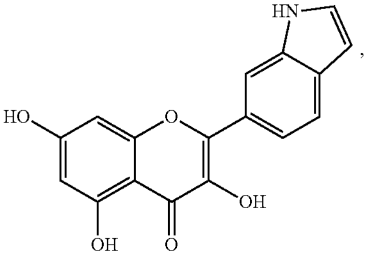
,
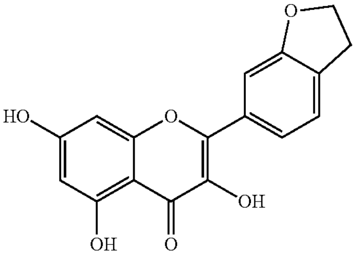
and
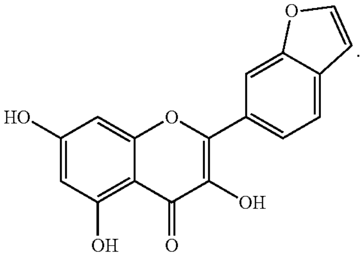
.
* * * * *